(12) United States Patent
Walker et al.

(10) Patent No.: US 9,062,047 B2
(45) Date of Patent: Jun. 23, 2015

(54) CRYSTALLINE FORM OF PYRIMIDO[6,1-A] ISOQUINOLIN-4-ONE COMPOUND

(75) Inventors: Michael J. A. Walker, Vancouver (CA); Bertrand M. C. Plouvier, Vancouver (CA); Julian S. Northen, Sunderland (GB); Philippe Fernandes, Sunderland (GB)

(73) Assignee: Verona Pharma plc, London (GB)

( * ) Notice: Subject to any disclaimer, the term of this patent is extended or adjusted under 35 U.S.C. 154(b) by 12 days.

(21) Appl. No.: 13/814,877

(22) PCT Filed: Aug. 9, 2011

(86) PCT No.: PCT/EP2011/063694
§ 371 (c)(1),
(2), (4) Date: May 15, 2013

(87) PCT Pub. No.: WO2012/020016
PCT Pub. Date: Feb. 16, 2012

(65) Prior Publication Data
US 2013/0225616 A1    Aug. 29, 2013

Related U.S. Application Data

(60) Provisional application No. 61/371,892, filed on Aug. 9, 2010.

(51) Int. Cl.
*A61K 31/519* (2006.01)
*C07D 471/04* (2006.01)
*A61K 45/06* (2006.01)

(52) U.S. Cl.
CPC ............ *C07D 471/04* (2013.01); *A61K 31/519* (2013.01); *A61K 45/06* (2013.01)

(58) Field of Classification Search
CPC .......................... A61K 31/519; C07D 471/04
See application file for complete search history.

(56) References Cited

FOREIGN PATENT DOCUMENTS

| WO | 00/58308 A1 | 10/2000 |
| WO | WO 2009011893 A2 * | 1/2009 |

OTHER PUBLICATIONS

COPD Foundation. "What is COPD?" © 2014. Available from: < http://www.copdfoundation.org/What-is-COPD/Understanding-COPD/What-is-COPD.aspx >.*
WebMD. "COPD—Medications." © 2012. Available from: < http://www.webmd.com/lung/copd/tc/chronic-obstructive-pulmonary-disease-copd-medications >.*
M.R. Caira, "Crystalline Polymorphism of Organic Compounds", Topics in Current Chemistry, vol. 198, pp. 163-208 (1998).
Franciosi, Lui G. et al., "Efficacy and safety of RPL554, a dual PDE3 and PDE4 inhibitor, in healthy volunteers and in patients with asthma or chronic obstructive pulmonary disease: findings from four clinical trials," www.thelancet.com/respiratory (published online Oct. 25, 2013) http://dx.doi.org/10.1016/S2213-2600(13)70187-5, 14 pages.
JP Version: Hirayama, Nriaki, "Organic compound crystal preparation handbook —principles and know-how," Maruzen Co., Ltd. (2008) pp. 37-40, 46, 57-65; see brief description included with certification.

* cited by examiner

*Primary Examiner* — Noble Jarrell
*Assistant Examiner* — John S Kenyon
(74) *Attorney, Agent, or Firm* — Kilpatrick Townsend & Stockton LLP

(57) ABSTRACT

The current invention is directed towards a polymorph of N-{2-[(2E)-2-(mesitylimino)-9,10-dimethoxy-4-oxo-6,7-dihydro-2H-pyrimido[6,1-a]-isoquinolin-3(4H)-yl]ethyl}urea, in the form of a crystalline solid consisting of greater than 99% by weight of N-{2-[(2E)-2-(mesitylimino)-9,10-dimethoxy-4-oxo-6,7-dihydro-2H-pyrimido[6,1-a]-isoquinolin-3(4H)-yl]ethyl}urea, at least 95% in the polymorphic form of a thermodynamically stable polymorph (I) of N-{2-[(2E)-2-(mesitylimino)-9,10-dimethoxy-4-oxo-6,7-dihydro-2H-pyrimido[6,1-a]-isoquinolin-3(4H)-yl]ethyl}urea, wherein said polymorph is determined by single crystal X-ray structural analysis and X-ray powder diffraction pattern.

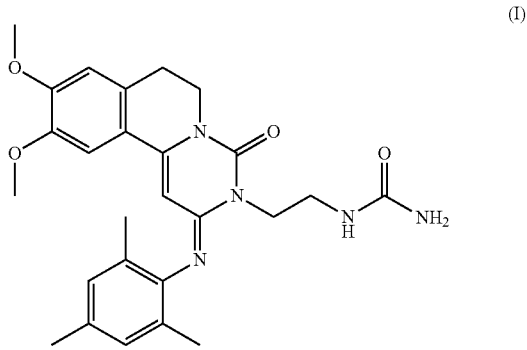

25 Claims, 12 Drawing Sheets

CRYSTALLINE FORM OF PYRIMIDO[6,1-A] ISOQUINOLIN-4-ONE COMPOUND

BACKGROUND OF THE INVENTION

The polymorphic behavior of drugs can be of crucial importance in pharmacy and pharmacology. Polymorphs are, by definition, crystals of the same molecule having different physical properties as a result of the order of the molecules in the crystal lattice. The differences in physical properties exhibited by polymorphs affect pharmaceutical parameters such as storage stability, compressibility and density (important in formulation and product manufacturing), and dissolution rates (an important factor in determining bio-availability). Differences in stability can result from changes in chemical reactivity (e.g. differential oxidation, such that a dosage form discolors more rapidly when comprised of one polymorph than when comprised of another polymorph) or mechanical changes (e.g. tablets crumble on storage as a kinetically favored polymorph converts to thermodynamically more stable polymorph) or both (e.g. tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing: for example, one polymorph might be more likely to form solvates or might be difficult to filter and wash free of impurities (i.e particle shape and size distribution might be different between one polymorph relative to the other).

Each pharmaceutical compound has an optimal therapeutic blood concentration and a lethal concentration. The bio-availability of the compound determines the dosage strength in the drug formulation necessary to obtain the ideal blood level. If the drug can crystallize as two or more polymorphs differing in bio-availability, the optimal dose will depend on the polymorph present in the formulation. Some drugs show a narrow margin between therapeutic and lethal concentrations. Chloramphenicol-3-palmitate (CAPP), for example, is a broad spectrum antibiotic known to crystallize in at least three polymorphic forms and one amorphous form. The most stable form, A, is marketed. The difference in bio-activity between this polymorph and another form B, is a factor of eight—creating the possibility of fatal overdosages of the compound if unwittingly administered as form B due to alterations during processing and/or storage. Therefore, regulatory agencies, such as the US Food and Drug Administration, have begun to place tight controls on the polymorphic content of the active component in solid dosage forms. In general, for drugs that exist in polymorphic forms, if anything other than the pure, thermodynamically preferred polymorph is to be marketed, the regulatory agency will require batch-by-batch monitoring. Thus, it becomes important for both medical and commercial reasons to produce and market the pure drug in its most thermodynamically stable polymorph, substantially free of other kinetically favored polymorphs.

U.S. Pat. Nos. 6,794,391, 7,378,424, and 7,105,663, which are each incorporated herein by reference, discloses compound RPL-554 (N-{2-[(2E)-2-(mesitylimino)-9,10-dimethoxy-4-oxo-6,7-dihydro-2H-pyrimido[6,1-a]-isoquinolin-3 (4H)-yl]ethyl}urea).

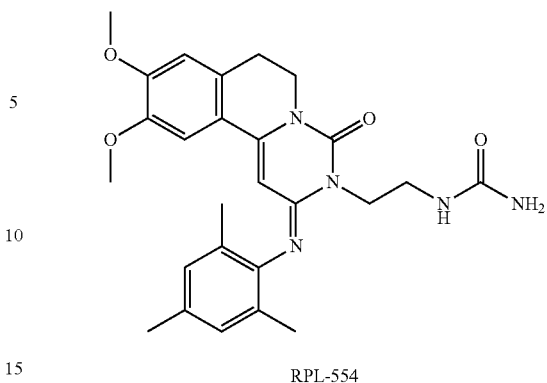

RPL-554

It would be beneficial to provide a composition of a stable polymorph of RPL-554, that has advantages over less stable polymorphs or amorphous forms, including stability, compressibility, density, dissolution rates, increased potency or, lack of toxicity.

SUMMARY OF THE INVENTION

In one aspect, the invention provides a polymorphic form of N-{2-[(2E)-2-(mesitylimino)-9,10-dimethoxy-4-oxo-6,7-dihydro-2H-pyrimido[6,1-a]-isoquinolin-3(4H)-yl] ethyl}urea (RPL-554). As a result of its unique stability properties, this polymorph provides a highly pure N-{2-[(2E)-2-(mesitylimino)-9,10-dimethoxy-4-oxo-6,7-dihydro-2H-pyrimido[6,1-a]-isoquinolin-3(4H)-yl]ethyl}urea in its most thermodynamically stable polymorphic form.

In another aspect, the invention provides a compound N-{2-[(2E)-2-(mesitylimino)-9,10-dimethoxy-4-oxo-6,7-dihydro-2H-pyrimido[6,1-a]-isoquinolin-3(4H)-yl] ethyl}urea, in the form of a crystalline solid consisting of greater than 99% by weight of N-{2-[(2E)-2-(mesitylimino)-9,10-dimethoxy-4-oxo-6,7-dihydro-2H-pyrimido[6,1-a]-isoquinolin-3(4H)-yl]ethyl}urea, at least 95% in the polymorphic form of a thermodynamically stable polymorph (I) of N-{2-[(2E)-2-(mesitylimino)-9,10-dimethoxy-4-oxo-6,7-dihydro-2H-pyrimido[6,1-a]-isoquinolin-3(4H)-yl]ethyl}urea, said polymorph (I) having the following structural parameters obtained by single crystal analysis:

| | |
|---|---|
| Wavelength | 0.71073 Å |
| Crystal system | Triclinic |
| Space group | P-1 |
| Unit cell dimensions | a = 8.1246(4) Å   α = 91.583(4)°. |
| | b = 11.4573(5) Å   β = 90.299(4)°. |
| | c = 13.2398(6) Å   γ = 99.628(4)°. |
| Volume | 1214.56(10) Å$^3$ |
| Z | 2. |

In another aspect, the invention provides a crystalline polymorph (1) of N-{2-[(2E)-2-(mesitylimino)-9,10-dimethoxy-4-oxo-6,7-dihydro-2H-pyrimido[6,1-a]-isoquinolin-3 (4H)-yl]ethyl}urea having a powder X-ray diffraction pattern comprising characteristic peaks, in terms of 2θ, at about 10.1° and about 12.9°.

In certain embodiments, said powder X-ray diffraction pattern further comprises characteristics peaks, in terms of 2θ, at about 15.3° and about 17.6°.

In another embodiment, said powder X-ray diffraction pattern comprises at least 5 characteristic peaks, in terms of 2θ, selected from about 6.4°, about 10.1°, about 12.6°, about 12.9°, about 13.6°, about 14.2°, about 14.7°, about 15.3°, about 15.4°, about 15.8°, about 17.0°, about 17.6°, about 18.9°, about 20.9°, about 22.4°, about 22.8°, and about 28.7°.

In certain embodiments, the polymorph has a powder X-Ray diffraction pattern substantially as shown in FIG. 1.

In other embodiments, the polymorph has a differential scanning calorimetry trace showing a maximum at about 248° C.

In various embodiments, the polymorph has a differential scanning calorimetry trace substantially as shown in FIG. 4.

In another aspect, the invention provides a solid composition comprising the polymorph as described herein.

In one embodiment, the invention provides a composition wherein at least about 50% by weight of total N-{2-[(2E)-2-(mesitylimino)-9,10-dimethoxy-4-oxo-6,7-dihydro-2H-pyrimido[6,1-a]-isoquinolin-3(4H)-yl]ethyl}urea in said composition is present as said polymorph.

In other embodiments, the invention provides a composition wherein at least about 70% by weight of total N-{2-[(2E)-2-(mesitylimino)-9,10-dimethoxy-4-oxo-6,7-dihydro-2H-pyrimido[6,1-a]-isoquinolin-3(4H)-yl]ethyl}urea in said composition is present as said polymorph.

In other embodiments, the invention provides a composition wherein at least about 90% by weight of total N-{2-[(2E)-2-(mesitylimino)-9,10-dimethoxy-4-oxo-6,7-dihydro-2H-pyrimido[6,1-a]-isoquinolin-3(4H)-yl]ethyl}urea in said composition is present as said polymorph.

In other embodiments, the invention provides a composition wherein at least about 97% by weight of total N-{2-[(2E)-2-(mesitylimino)-9,10-dimethoxy-4-oxo-6,7-dihydro-2H-pyrimido[6,1-a]-isoquinolin-3(4H)-yl]ethyl}urea in said composition is present as said polymorph.

In another embodiment, the invention provides a solid composition comprising the polymorph as described above and, a pharmaceutically acceptable carrier.

In certain embodiments, the solid composition comprises the polymorph and one or more additional compounds.

In a further embodiment, the additional compound is a known therapeutic.

In certain embodiments, the therapeutic is used to treat asthma, allergic asthma, hay fever, allergic rhinitis, bronchitis, chronic obstructive pulmonary disease (COPD), adult respiratory distress syndrome (ARDS), cystic fibrosis, skin disorders, atopic dermatitis, psoriasis, ocular inflammation, cerebral ischaemia, or auto-immune diseases.

In other embodiments, the invention provides a solid composition wherein the therapeutic is used to treat asthma or COPD.

In certain aspects, the invention provides a process for preparing the polymorph of the invention comprising:
(a) combining N-{2-[(2E)-2-(mesitylimino)-9,10-dimethoxy-4-oxo-6,7-dihydro-2H-pyrimido[6,1-a]-isoquinolin-3(4H)-yl]ethyl}urea with a solvent to form a mixture, and
(b) heating at or above a temperature of about 50° C. for a time and under conditions suitable for forming said polymorph.

In certain aspects, the invention provides a process for preparing the polymorph of the invention comprising:
(a) combining N-{2-[(2E)-2-(mesitylimino)-9,10-dimethoxy-4-oxo-6,7-dihydro-2H-pyrimido[6,1-a]-isoquinolin-3(4H)-yl]ethyl}urea with a solvent to form a mixture,
(b) filtration of said mixture,
(c) heating at or above a temperature of about 55° C. for a time and under conditions suitable for forming said polymorph; and
(d) filtration and drying.

In certain embodiments, the solvent is DMSO, ethanol, methanol, isopropanol, hexanes, pentane, ethyl acetate, dichloromethane, or chloroform. In a further embodiment, the solvent is DMSO or ethanol.

In another embodiment, said mixture is maintained at or above a temperature of about 50° C. for about 24 to 96 hours. In a further embodiment, said mixture is maintained at or above a temperature of about 50° C. for about 72 hours. In other embodiments, said mixture is maintained at or above a temperature of about 55° C. for about 24 to 96 hours. In various embodiments, said mixture is maintained at or above a temperature of about 55° C. for about 72 hours.

In other embodiments, said mixture is dried in vacuo at between 25 and 50° C. In a further embodiment, said mixture is dried in vacuo at 40° C.

In another embodiment, the invention provides for a polymorph as described above, prepared by the method comprising
(a) combining N-{2-[(2E)-2-(mesitylimino)-9,10-dimethoxy-4-oxo-6,7-dihydro-2H-pyrimido[6,1-a]-isoquinolin-3(4H)-yl]ethyl}urea with a solvent to form a mixture, and
(b) heating at or above a temperature of about 50° C. for a time and under conditions suitable for forming said polymorph.

In another embodiment, the invention provides for a polymorph as described above prepared by the method comprising
(a) combining N-{2-[(2E)-2-(mesitylimino)-9,10-dimethoxy-4-oxo-6,7-dihydro-2H-pyrimido[6,1-a]-isoquinolin-3(4H)-yl]ethyl}urea with a solvent to form a mixture,
(b) filtration of said mixture,
(c) heating at or above a temperature of about 55° C. for a time and under conditions suitable for forming said polymorph; and
(d) filtration and drying.

In another aspect, the invention provides a method to treat asthma, allergic asthma, hay fever, allergic rhinitis, bronchitis, chronic obstructive pulmonary disease (COPD), adult respiratory distress syndrome (ARDS), cystic fibrosis, skin disorders, atopic dermatitis, psoriasis, ocular inflammation, cerebral ischaemia, or auto-immune diseases, in a mammal in need thereof, which method comprises administering to said mammal an effective amount of a crystalline polymorph of N-{2-[(2E)-2-(mesitylimino)-9,10-dimethoxy-4-oxo-6,7-dihydro-2H-pyrimido[6,1-a]-isoquinolin-3(4H)-yl]ethyl}urea.

In one embodiment, the mammal is a human.

The amorphous form of RPL554 is less stable as it may transform in varying extents to various polymorph forms under certain conditions and may transform on storage. It would also be more demanding to produce in a large scale the amorphous form consistently within the required cGMP specifications in terms of purity as well as the impurity profile. The amorphous form therefore presents challenges in the development of a reproducible uniform micronized dry solid powder of RPL554 for certain formulation applications. Whereas crystalline polymorph Form I can be more readily manufactured on a large cGMP scale to provide solid RPL554 as an active pharmaceutical ingredient (API) in a more consistent and reproducible process. The purification and isolation processes for crystalline polymorph Form I product are more amenable for large scale cGMP production. The above advantages result in providing product batches that are consistently within the required cGMP specifications. As shown in one aspect of this invention, crystalline polymorph Form I is the most thermodynamically stable polymorphic form of RPL554 and is also expected to have the longest shelf life on storage. This advantage should extend further to the potential shelf life of any commercial RPL554 drug product containing the stable crystalline polymorph Form I as an API. Furthermore crystalline polymorph Form I is more amenable for the development of a reproducible uniform micronized dry solid powder of RPL554 for certain pharmaceutical formulation applications.

The study of N-{2-[(2E)-2-(mesitylimino)-9,10-dimethoxy-4-oxo-6,7-dihydro-2H-pyrimido[6,1-a]-isoquinolin-3(4H)-yl]ethyl}urea (RPL554), presented in a crystalline form (designated Form I), showed that the material was very resilient to change and that Form I was, within the limits of the study performed, the most stable polymorphic form of the material known (see experimental).

A range of experimentation was applied in order to discover the existence of new, pure polymorphs of the compound, these being: Anti-solvent addition; Saturated solution work; Slurry maturation; Formal recrystallisation; Mixed solvent studies; and Aqueous system crystallisation.

Generation of the amorphous phase was accomplished and this also used in some of the studies with similarly conclusive results, in that Form I predominated with the exception of only a few experiments where change was induced. In the cases where change was induced on a small-scale, attempts were made to scale up the crystallisations in order to fully characterise the forms (pure and mixed), to determine whether this change was due to solvation or a non-solvated entity. In most cases, due to the delicate nature of the process variables required to repeat such crystallisations and the overall stabilities of the systems, Form I was returned. The main exception was DMSO, where a potential higher melting phase was observed as a mixture with Form I, post main melt within the decomposition cycle for the material. It was also notable that DMSO returned two other altered phases prior to this scale-up, each different, but ultimately representative of what was most likely a less stable form and/or solvate.

Previous reports suggested that amorphous material could be generated by crash cooling a melt. Rapid evaporation from DCM provided a robust method, whereas crash cooling a melt simply resulted in decomposition (amorphous by XRPD, but <20% product by HPLC analysis).

As historically it was not known whether the process derived material produced in-house was amorphous or crystalline solubility trials were repeated for both of these materials to act as a guide, with the amorphous phase proving to be more soluble.

Ultimately, Form I was shown as the thermodynamically favored phase and as an aside, that manipulation of either the crystalline or amorphous material could be successfully achieved with reference to altered physical presentation of the materials isolated e.g. powder vs larger crystalline aspect.

Of significance during the progression of this material was that applied pressure resulted in the generation of what was presumed to be amorphous material, as indicated by XRPD and DSC. The thermal profile for this material showed a noted exothermic crystallisation and subsequent melting endotherm that was very close to that Form I. This could be verified by repeating with more material and isolating the product post exothermic event and checking by XRPD and HPLC.

DETAILED DESCRIPTION OF THE INVENTION

Figure 1:
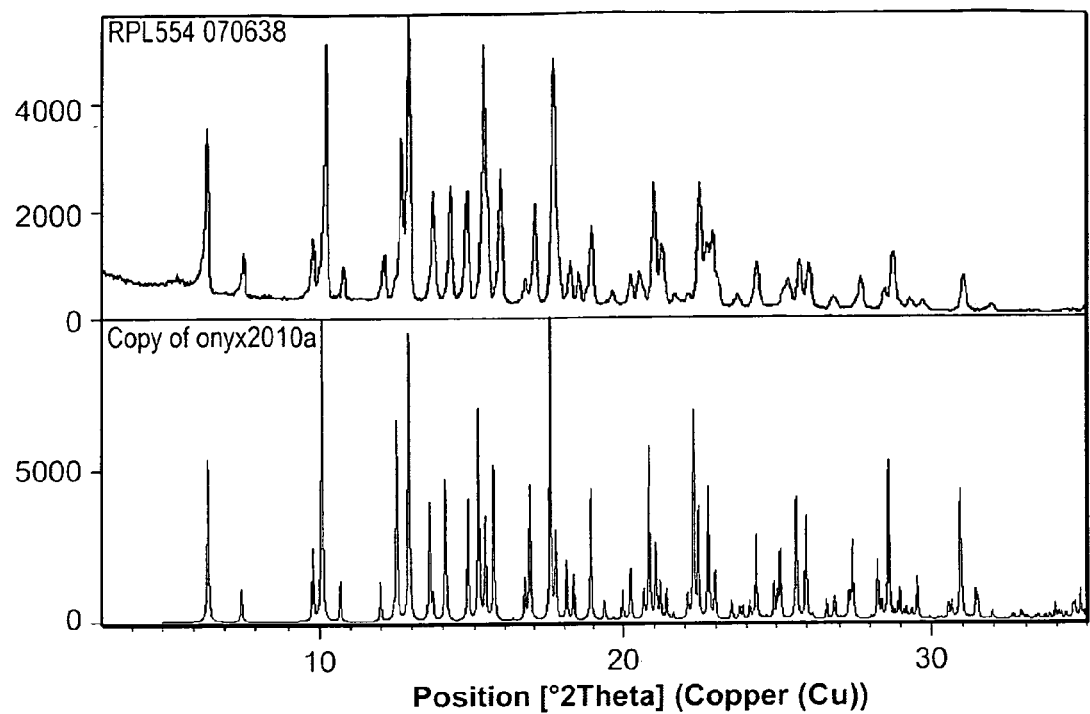
FIG. 1: Comparison of RPL554 measured data (top) vs simulated single crystal data (bottom).

The study of N-{2-[(2E)-2-(mesitylimino)-9,10-dimethoxy-4-oxo-6,7-dihydro-2H-pyrimido[6,1-a]-isoquinolin-3(4H)-yl]ethyl}urea (RPL554), presented in a crystalline form (designated Form I), showed that the material was very resilient to change and that Form I was, within the limits of the study performed, the most stable polymorphic form of the material known. A range of experimentation was applied in order to test this, including within such studies the use of amorphous material. Both phases, upon production, showed that Form I predominated with the exception of only a few experiments where change was induced. In the cases where change was induced on a small-scale, attempts were made to scale up the crystallisations in order to fully characterise the forms (pure and mixed), to determine whether change was due to solvation or a non-solvated entity. In most cases, due to the delicate nature of the process variables required to repeat such crystallisations and the overall stabilities of the systems, Form I was returned. The main exception was DMSO, where a potential higher melting phase was observed as a mixture with Form I, post main melt within the decomposition cycle for the material.

Previous reports suggested that amorphous material could be generated by crash cooling a melt. Rapid evaporation from DCM provided a robust method, whereas crash cooling a melt simply resulted in decomposition (amorphous by XRPD, but <20% product by HPLC analysis).

As historically it was not known whether the process derived material produced in-house was amorphous or crystalline, solubility trials were repeated for both of these materials to act as a guide.

Ultimately, Form I was shown as the thermodynamically favored phase and that manipulation of either the crystalline or amorphous material could be successfully achieved with reference to altered physical presentation of the materials isolated e.g. powder vs larger crystalline aspect. On this basis 3 trial crystallisations were started with the aim of growing material suitable for single crystal analysis and to complement the indexing and unit cell refinement performed with the high quality powder data obtained.

X-ray powder diffraction is the ideal tool for obtaining a fingerprint of the pharmaceutical product of interest. Ideally, the powder data will relate to a unique crystalline form with a unique XRPD. Because of the collapse of crystallographic information from 3D to 2D, a typical XRPD will see the overlap of diffracting peaks at high two theta values. Due to this fact, indexing a powder pattern (relating the data to unit cell parameters) remains a challenging step, although vast progress has been accomplished over the recent years.

The data presented herein potentially relates to the correct unit cell parameters of RPL554. The algorithm in the software allows the output of unit cell settings with figures of merit. The higher these values are, the higher the chances in obtaining the correct unit cell.

X-Ray Powder Diffraction (XRPD) PANalytical X'Pert PRO: X-Ray Powder Diffraction patterns were collected on a PANalytical diffractometer using Cu K$\alpha$ radiation (45 kV, 40 mA), $\theta$-$\theta$ goniometer, focusing mirror, divergence slit (½"), soller slits at both incident and divergent beam (4 mm) and a PIXcel detector. The software used for data collection was X'Pert Data Collector, version 2.2f and the data was presented using X'Pert Data Viewer, version 1.2d.

Samples were run under ambient conditions and were analysed by transmission foil XRPD, using the powder as received. Approximately 2-5 mg of the sample was mounted on a 96 position sample plate supported on a polyimide (Kapton, 12.7 μm thickness) film. Data was collected in the range 3-40° 2θ with a continuous scan (speed of 0.146° 2θ/s).

Differential Scanning calorimetry (DSC): DSC data was collected on a PerkinElmer Pyris 4000 DSC. The instrument was verified for energy and temperature calibration using certified indium. A predefined amount in milligrams mg of the sample was placed in a pin holed aluminium pan and typically heated at 20° C.·min$^{-1}$ from 30° C. to 350° C., or varied as experimentation dictated. The instrument control and data analysis was Pyris Software v9.0.1.0174.

Thermo-Gravimetric Analysis (TGA): TGA data were collected on a Pyris 1 TGA equipped with a 20 position autosampler. The instrument was calibrated using certified indium. A predefined amount in milligrams of the sample was loaded onto a pre-weighed aluminium crucible and was heated at 40° C. min$^{-1}$ from ambient temperature to 400° C. A nitrogen purge at 20 ml min$^{-1}$ was maintained over the sample. The instrument control and data analysis was Pyris Software v9.0.1.0174.

Gravimetric Vapour Sorption: Sorption isotherms are obtained using a Hiden Isochema moisture sorption analyser (model IGAsorp), controlled by IGAsorp Systems Software V6.50.48. The sample was maintained at a constant temperature (25° C.) by the instrument controls. The humidity was controlled by mixing streams of dry and wet nitrogen, with a total flow of 250 ml min$^{-1}$. The instrument was verified for relative humidity content by measuring three calibrated Rotronic salt solutions (10-50-88%). The weight change of the sample was monitored as a function of humidity by a microbalance (accuracy+/−0.005 mg). A defined amount of sample was placed in a tared mesh stainless steel basket under ambient conditions. A full experimental cycle consisted of two scans (sorption and desorption) at a constant temperature (25° C.) and 10% RH intervals over a 10-90% range (90 minutes for each humidity level). This type of experiment should demonstrate the ability of samples studied to absorb moisture (or not) over a set of well determined humidity ranges.

Nuclear Magnetic Resonance (NMR) $^1$H: NMR spectra were collected on a Bruker 270 MHz instrument equipped with an auto-sampler and controlled by a DRX400 console. Automated experiments were acquired using Delta NMR Processing & Control Software version 4.3. Samples were prepared in d6-DMSO, unless otherwise stated. Analysis was carried out using (ACD/Specmanager 7.11).

Thermodynamic Aqueous Solubility by HPLC: Aqueous solubility was determined by suspending sufficient compound in HPLC grade water to give a maximum final concentration of ≥20 mg ml$^{-1}$ of the parent compound. The suspension was equilibrated at 25° C. for 24 hours. The suspension was then filtered through a filter into a HPLC vial. The filtrate was then diluted by an appropriate factor. Quantification was executed by HPLC with reference to a standard solution of approximately 0.5 mg ml$^{-1}$ in Acetonitrile:Water: (1:1). Different volumes of the standard, diluted and undiluted sample solutions were injected. The solubility was calculated using the peak areas determined by integration of the peak found at the same retention time as the principal peak in the standard injection.

Analysis was performed on an Agilent 1100 series liquid chromatography, equipped with a UV detector (DAD or VWD) @254 nm and using Chemstation Rev.B.01.03 software for data processing. Chemical purity determination by HPLC.

Pharmaceutical Compositions

The pharmaceutical compositions of the present invention comprise a therapeutically effective amount of a polymorph of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray. Other routes of drug administration include inhalation of medicament from a solution or suspension of the pharmaceutical compositions of the present invention in a metered dose inhaler (MDI) or a nebulizer, or inhalation of powdered drug comprising a therapeutically effective amount of a polymorph of the present invention generally admixed with an excipient or the pharmaceutical compositions of the present invention, from a dry powder inhaler (DPI).

Liquid dosage forms for oral administration include pharmaceutically acceptable emulsions, microemulsions, solutions, suspensions, syrups, and elixirs. In addition to the active compounds, the liquid dosage forms may contain inert diluents commonly used in the art such as, for example, water, alcohol or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, polysorbate, dimethylformamide, oils (in particular, cottonseed, groundnut, corn, germ, olive, castor, and sesame oils), mono- or di-glycerides, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, antioxidants, sweetening, flavoring, and perfuming agents. The liquid dosage form can also be encapsulated in a gelatin capsule, wherein a compound of the present invention can be dissolved in a pharmaceutically acceptable carrier containing, for example, one or more solubilizating agents (e.g., polysorbate 80 and mono and diglycerides), and other suitable excipients (e.g., an antioxidants such as ascorbyl palmitate, or a sweetening or flavoring agent).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Immediate release forms are also contemplated by the present invention.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound polymorph.

Solid compositions of a similar type may also be employed as fillers in soft and hard-filled gelatin capsules using such excipients as lactose or milk sugar as well as high molecular weight polyethylene glycols and the like.

The active polymorphs can also be in micro-encapsulated form with one or more excipients as noted above.

The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Preferably, a polymorph of the invention is formulated in a solid dispersion, where the polymorph can be molecularly dispersed in a matrix which comprises a pharmaceutically acceptable, hydrophilic polymer. The matrix may also contain a pharmaceutically acceptable surfactant. Suitable solid dispersion technology for formulating a polymorph of the invention includes, but is not limited to, melt extrusion, spray drying, or solvent evaporization.

Dosage forms for topical or transdermal administration of a polymorph of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to a polymorph of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the polymorphs of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a polymorph to the body. Such dosage forms can be made by dissolving or dispensing the polymorph in the proper medium. Absorption enhancers can also be used to increase the flux of the polymorph across the skin. The rate can be controlled by either providing a rate controlling membrane or by dispersing the compound in a polymer matrix or gel.

Biological Activity

In another aspect, the present invention provides a polymorph composition comprising a polymorph of the invention and a veterinarily or pharmaceutically acceptable carrier or diluent. Preferably the composition is a pharmaceutical composition for human medicine. In another aspect, the composition of the present invention is a composition for veterinary medicine.

The polymorph compounds of the present invention are PDE inhibitors and thus possess valuable pharmacological properties, such as bronchodilator activity as demonstrated by the inhibition of field-stimulated contraction of guinea-pig isolated trachea, and anti-inflammatory activity as illustrated in studies on human mononuclear cells stimulated by PHA (phytohaemagglutinin). In vitro and in vivo data indicate the compounds have a long duration of action, as demonstrated by their persistent protective effects against histamine induced bronchospasm in the guinea-pig when inhaled directly into the lungs as a dry powder. The invention therefore also relates to acute, chronic or prophylactic treatment of patients suffering from respiratory disorders including, in particular, asthma, allergic asthma, hay fever, allergic rhinitis, bronchitis, chronic obstructive pulmonary disease (COPD), adult respiratory distress syndrome (ARDS), and cystic fibrosis. They may also be used topically in skin disorders such as atopic dermatitis and psoriasis, or in ocular inflammation or any other disease including cerebral ischaemia or auto-immune diseases in which increasing intracellular concentrations of cAMP is considered beneficial.

One or more compound polymorphs may be present in association with one or more non-toxic pharmaceutically and/or veterinarily acceptable carriers and/or diluents and/or adjuvants and/or propellants and, if desired, other active ingredients. Suitable carriers or diluents are known in the art (eg Handbook of Pharmaceutical Excipients (1994) 2nd Edition, Eds. A. Wade/PJ Weller, The Pharmaceutical Press, American Pharmaceutical Association).

According to another aspect, the present invention provides a compound polymorph for use in medicine. Polymorph compounds of the present invention are useful as inhibitors of phosphodiesterase isoenzymes. The polymorphs of the compounds or compositions of the present invention may be used to prevent or treat any disease in which the compounds or compositions are useful, but particularly a disease in which raising the intracellular concentration of cAMP is desirable. Examples of diseases against which compounds are useful include respiratory disorders including, in particular, asthma, bronchitis, chronic obstructive pulmonary disease (COPD), adult respiratory distress syndrome (ARDS), allergic asthma, hay fever, allergic rhinitis, and cystic fibrosis. They may also be used topically in skin disorders such as atopic dermatitis or psoriasis, ocular inflammation, or any other disease including cerebral ischaemia or auto-immune diseases in which increasing intracellular concentrations of cAMP is considered beneficial.

This aspect of the invention is particularly relevant to the treatment of humans, but is also applicable to general veterinary industry, in particular domestic animals such as dogs and cats and farm animals such as horses, pigs, cattle, sheep, etc.

Dosage levels of the order of about 0.02 mg to about 200 mg, to be taken up to three times daily, are useful in the treatment of the above-mentioned conditions. More particularly, a dosage range of about 0.2 mg to about 20 mg, taken up to three times daily, is effective. The particular dosage regime will however ultimately be determined by the attending physician and will take into consideration such factors as the medication being used, age, weight, severity of symptoms and/or severity of treatment being or to be applied, method of administration of the medication, adverse reactions and/or other contraindications.

The medication according to this aspect of the invention may be given to a patient together with other active agents, which may for example be a different compound or polymorph of the present invention, or other compounds. Examples include β2-adrenoceptor agonists, topical glucocorticoid steroids, xanthine derivatives, antihistamine compounds, leukotriene antagonists, inhibitors of leukotriene synthesis and/or combinations thereof.

According to another aspect, the present invention provides the use of a polymorph of the invention in the manufacture of an inhibitor of a type III/IV phosphodiesterase isoenzyme (PDE3/4). The invention encompasses the use of a polymorph of the invention in the manufacture of a bronchodilator and/or an anti-asthmatic medication and/or a medicament for the prevention or treatment of chronic obstructive pulmonary disease (COPD).

The invention also relates to a method for the treatment or prevention of a disease in a mammal where a phosphodiesterase isoenzyme inhibitor and/or a bronchodilator would be expected to be of benefit, which method comprises administering to said mammal an amount of an effective, non-toxic amount of a polymorph of the invention. The invention encompasses a method of treating or preventing asthma and/or chronic obstructive pulmonary disease (COPD) in a mammal.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Approximately 50 mg of N-{2-[(2E)-2-(mesitylimino)-9,10-dimethoxy-4-oxo-6,7-dihydro-2H-pyrimido[6,1-a]-isoquinolin-3(4H)-yl]ethyl}urea (RPL554) was dissolved in 0.5 ml of DMF at 70° C. The clear yellow solution was allowed to cool very slowly with nitrogen venting to approximately 30° C. over 4 days. An initial batch of material was observed within the liquors (approx. 0.4 ml) that was of a crystalline nature. This process was repeated twice and delivered material suitable for single crystal analysis within a liquor volume of approximately 0.2 ml. The sample was submitted for analysis unaltered within the mother liquor.

Single crystal data, was measured at low temperature (123 K) and at a different wavelength (0.71073 Å). In order to provide a picture that would give a direct comparison, manual adjustments on the wavelength value were necessary. After various adjustments, FIG. 1 was obtained and shows the split overlay between the measured data for RPL554 070638 via XRPD (top) and the simulated XRPD derived from single crystal data (Copy of onyx2010a, bottom).

Figure 2:
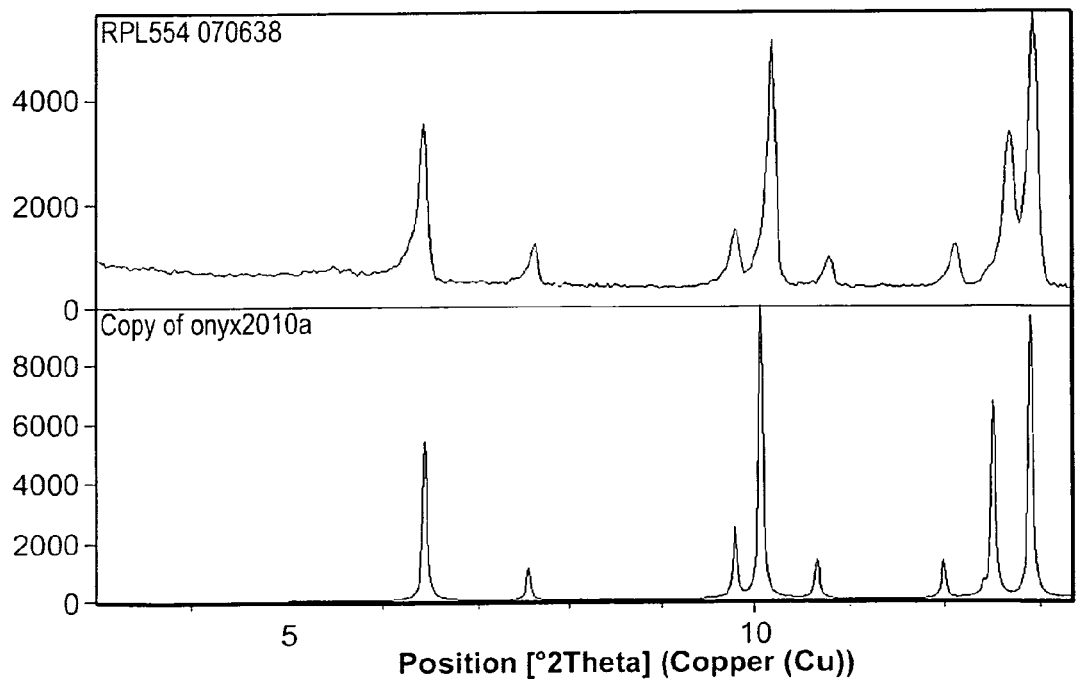
FIG. 2: Expansion comparison of the two theta range (5-13° 2θ).

A closer inspection (FIG. 2) in the two theta range (5-13° 2θ) clearly demonstrates the similarities between the observed data and the simulated powder pattern.

The algorithm in the software compares numerically the observed data (RPL554 070638) measured by transmission XRPD and the numerical values derived from the single crystal analysis. The key data derived from single crystal analysis is listed below:

| | |
|---|---|
| Temperature | 123(2) K |
| Wavelength | 0.71073 Å |
| Crystal system | Triclinic |
| Space group | P-1 |
| Unit cell dimensions | a = 8.1246(4) Å   α = 91.583(4)° |
| | b = 11.4573(5) Å   β = 90.299(4)° |
| | c = 13.2398(6) Å   γ = 99.628(4)° |
| Volume | 1214.56(10) Å$^3$ |
| Z | 2 |

The software applied for the comparison read the file measured (RPL554 070638) and prompted entry of the unit cell parameters extracted from the single crystal data. The Pawley refinement (algorithm) then returned numerical values, but the software also illustrates this numerical value by a graphical display of the result. The numerical value for the goodness of fit between measured and theoretical values for RPL554 was 2.9. This value expresses the data quality. The lower the value the better the data will be and usually a value less than 10 is considered as a positive hit.

The numerical values for RPL554 were in good agreement with the ones derived from the single crystal measured at 123K. Thus, the single crystal data provides an excellent match with the powder data collected for RPL554 in-house and is therefore representative of the crystallographic profile for the known thermodynamically favored polymorph (Form I).

Example 2

Starting Material

Figure 3:
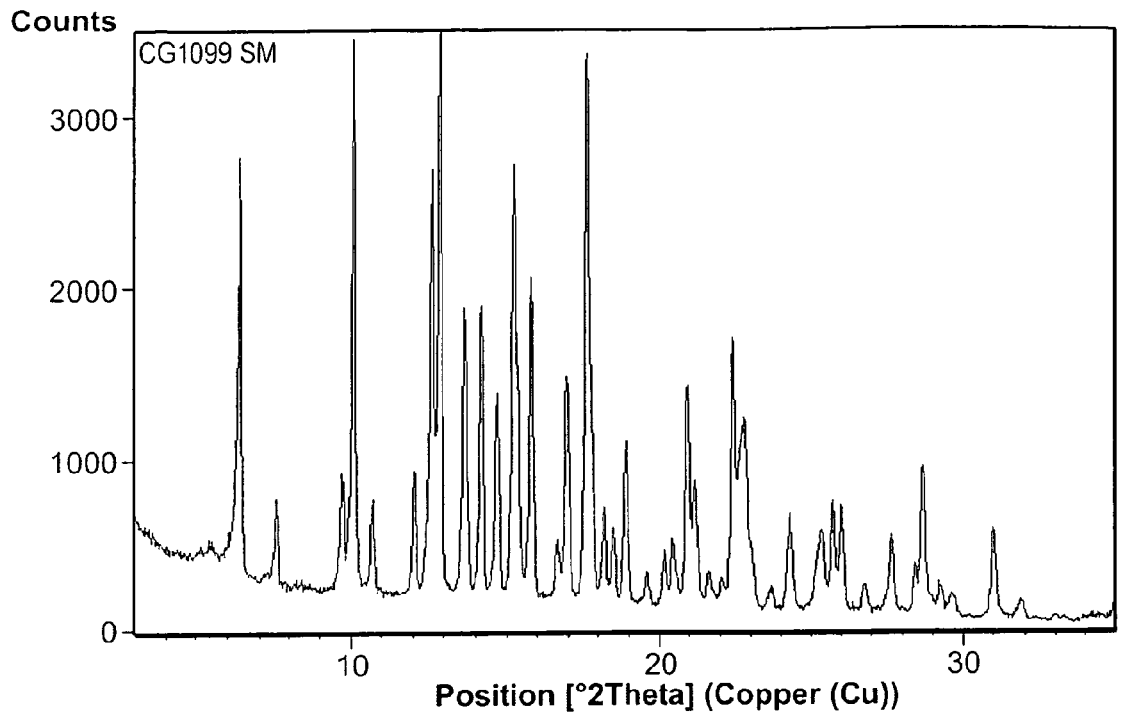
FIG. 3: Transmission XRPD profile for RPL554.
Figure 4:
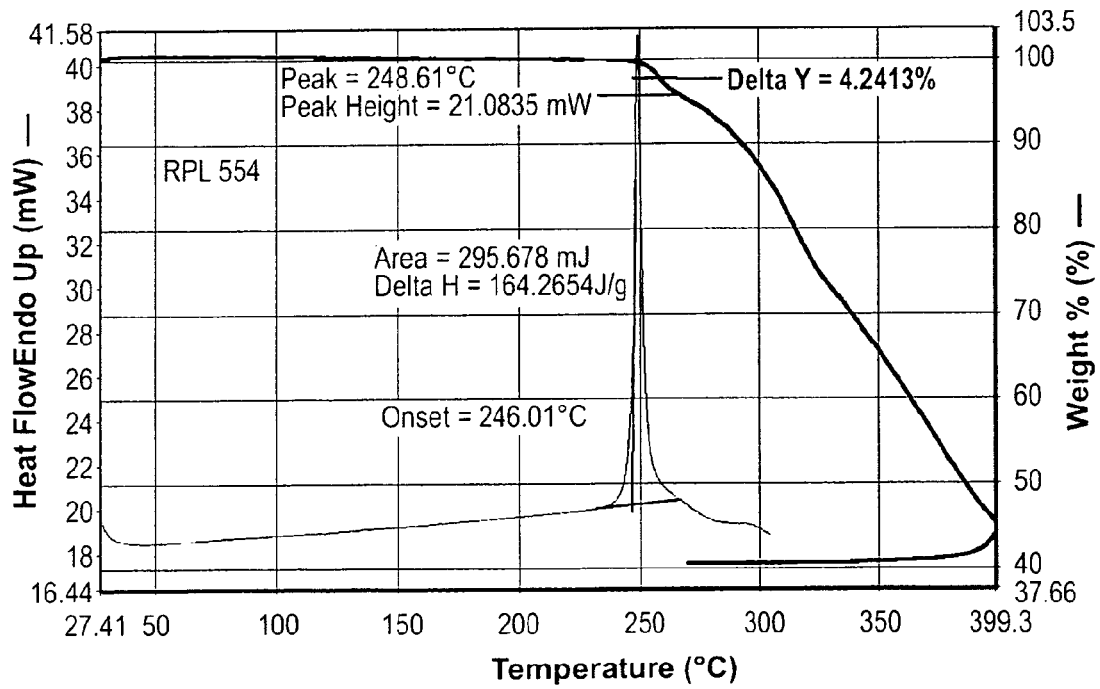
FIG. 4: DSC/TGA trace for RPL554.

A sample of 9.0 g ex-GMP stock of RPL554 (070638-9) was taken and analysed by XRPD (FIG. 3 and Table 1) and DSC (FIG. 4) for use as a current reference dataset.

TABLE 1

| Pos. [°2Th.] | Height [counts] |
| --- | --- |
| 6.3827 | 2406.64 |
| 10.1448 | 3293.52 |
| 12.6314 | 2495.28 |
| 12.8735 | 3362.54 |
| 13.6461 | 1682.38 |
| 14.2043 | 1714.62 |
| 14.7078 | 1191.12 |
| 15.2706 | 2566.43 |
| 15.4230 | 1230.41 |
| 15.8229 | 1877.13 |
| 16.9786 | 1303.49 |
| 17.6393 | 3211.22 |
| 18.8932 | 938.79 |
| 20.9592 | 1298.36 |
| 22.4382 | 1587.30 |
| 22.8201 | 1112.59 |
| 28.6947 | 876.91 |

Other studies such as proton NMR and HPLC at this juncture were not critical to the project initiation as results had been previously collected. Performing solubility studies on the material using a range of common organic materials was similarly unnecessary as previous studies had given a strong indication of the material behavior. Initiation of the investigation into the presence of other forms of RPL554 was the priority.

The material is, as known, crystalline with a melting onset of 246° C. for the single endotherm, with no subsequent crystallisation noted or transition, other than thermal decomposition. An initial weight loss of approximately 4.2% is noted by TGA, corresponding, to the melting endotherm, that is not solvent related (likely ammonia loss ahead of total fragmentation). Having obtained the reference data, experimentation with the material was initiated with the aim that amorphous material would subsequently be produced. From this juncture, the above data will be referred to as Form I.

It is assumed that the process to produce RPL554 delivers the material in the current form and that the slurries from alcohol used to improve its purity enhance its crystallinity, or more importantly, convert amorphous material into a crystalline form.

Example 3

Anti-solvent Addition

Anti-solvent addition is a well known method of obtaining amorphous material, new polymorphs and also mixed phases. With this in mind, a stock solution of RLP554 in DMSO was produced. DMSO was chosen as the material has reasonable solubility in this solvent, which is also widely miscible.

Experimental conditions (CG 1099):

300 mg of RPL554 was dissolved in hot DMSO (2 ml stock solution) and 0.15 ml of this solution added with vigorous stirring, in portions, to 12 cold tubes containing various solvents (1.0 ml) at room temperature. In almost all cases an instant precipitation was observed. Isolation was performed by filtration and drying in vacuo at 40° C. The results are detailed in the Table 2 below:

TABLE 2

Solvent list and details for DMSO based anti-solvent additions

| Solvent | Initial result | Isolated solids |
| --- | --- | --- |
| Cumene | sol$^n$ → ppt | F1 |
| nBuOAc | ppt | F1 |
| Dioxane | sol$^n$ | F1 on drying |
| Water | ppt | F1 |
| Heptane | Bi-layer/oil → ppt | F1 |
| IPA | ppt | F1 |
| $CH_3CN$ | ppt | F1 |
| MEK | ppt | F1 |
| EtOH | ppt | F1 |
| EtOAc | ppt | F1 |
| TBME | ppt | F1 |
| DCM | sol$^n$ | F1 on drying |

All of the samples that returned a solid, once dried in vacuo at 45° C. and analysed by XRPD showed that Form I had been returned. Notable exceptions were dioxane, DCM and heptane. Dioxane and DCM yielded solutions that were left to stand and evaporate, eventually yielding Form I.

Figure 5:
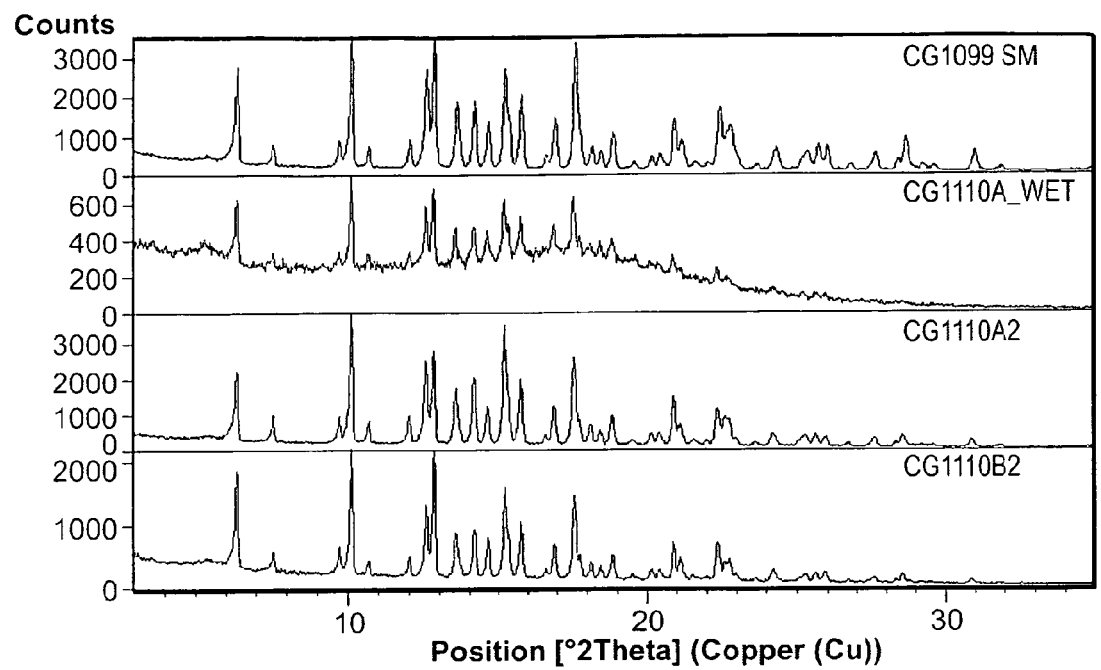
FIG. 5: XRPD comparisons of DMSO/heptane anti-solvent additions (CG1099)

Heptane was more interesting in that two layers formed, both coloured solutions, which gradually oiled upon extended shaking and resting periods (DMSO layer). After approximately 24 hours, solids had formed in the opaque oil and so the mixture was decanted and dried in vacuo at 45° C. Unfortunately, while it was hoped that amorphous material had been formed, Form I was observed. However, it was considered that a repeat of the experiment was warranted, but with less time allocated post formation of the precipitous oil. This again formed two clear layers and gradually resulted in a precipitous DMSO layer that was decanted and analysed both wet and dried (CG1110Awet and CG1110A2 respectively). The DMSO liquor was also allowed to reduce to a solid that was dried in vacuo (CG1110B2). The results are displayed in FIG. 5 showed that all samples were virtually identical to the starting material (CG1099SM).

Example 4

Saturated Solutions

Saturated solutions are by far the best method of obtaining pure phases of new polymorphs. Therefore, known amounts of RPL554 Form I were dissolved or slurried over time to obtain a saturated solution at temperature, followed by a polishing filtration to remove any form memory (seed). A controlled cool was then used to promote crystallisation.

Experimental (5N376):

24 Solvents were stirred at 45° C. in the presence of 30 mg of RPL554 Form I to leave an initial suspension. The suspensions were heated at 45° C. over a period of 4.5 hours before hot filtration into pre-warmed tubes that were then left to slowly evaporate ahead of drying in vacuo at 45° C. and analysis. Note that entries A and B (in Table 3) were warmed at 35° C. under nitrogen to aid evaporation for 24 hours.

TABLE 3

Solvent list and results for saturated solution experiments (JN376)

| Solvent | Grid entry | Observation | XRPD |
| --- | --- | --- | --- |
| Tetralin | A1 | Sol$^n$ → gum/oil | n/a |
| NMP | A2 | Fine XT growing | Form I |

TABLE 3-continued

Solvent list and results for saturated solution experiments (JN376)

| Solvent | Grid entry | Observation | XRPD |
|---|---|---|---|
| Ethylene glycol | A3 | insol | n/a |
| DMSO | A4 | Chunky XT growth | New Form DSC collected |
| Anisole | A5 | insol/trace oil | n/a |
| DMF | A6 | XT plus oil, oven dried | Form I |
| Cumene | B1 | insol | n/a |
| 3-Me-1-BuOH | B2 | Powder/gum, oven dried | Insufficient |
| n-BuOAc | B3 | insol/trace oil | n/a |
| Toluene | B4 | insol/trace oil | n/a |
| Dioxane | B5 | trace glass, oven dried | Form I |
| Water | B6 | insol | n/a |
| Heptane | C1 | insol | n/a |
| n-PrOH | C2 | trace powder | insufficient |
| IPA | C3 | trace powder | Form I |
| CH₃CN | C4 | Fine XT | Form I |
| MEK | C5 | trace powder | insufficient |
| EtOH | C6 | trace powder | Form I |
| EtOAc | D1 | insol | n/a |
| THF | D2 | insol | n/a |
| MeOH | D3 | insol | n/a |
| Acetone | D4 | insol | n/a |
| TBME | D5 | insol | n/a |
| DCM | D6 | powder | Form I |

Key:
XT = crystalline,
insol = insoluble/very little material,
trace powder-insufficient = not enough material to analyse From the table it can be seen that many of the experiments did not dissolve a sufficient amount of material to allow for analysis and returned either a speck of oil or powder at the bottom of the tube post drying. However, despite this a number of experiments returned material in powder form that allowed XRPD analysis to be collected. The most successful experiments, having shown formal crystals to be growing from the mother liquors, were harvested and only one entry showed any relevant form change (DMSO).

Figure 6:
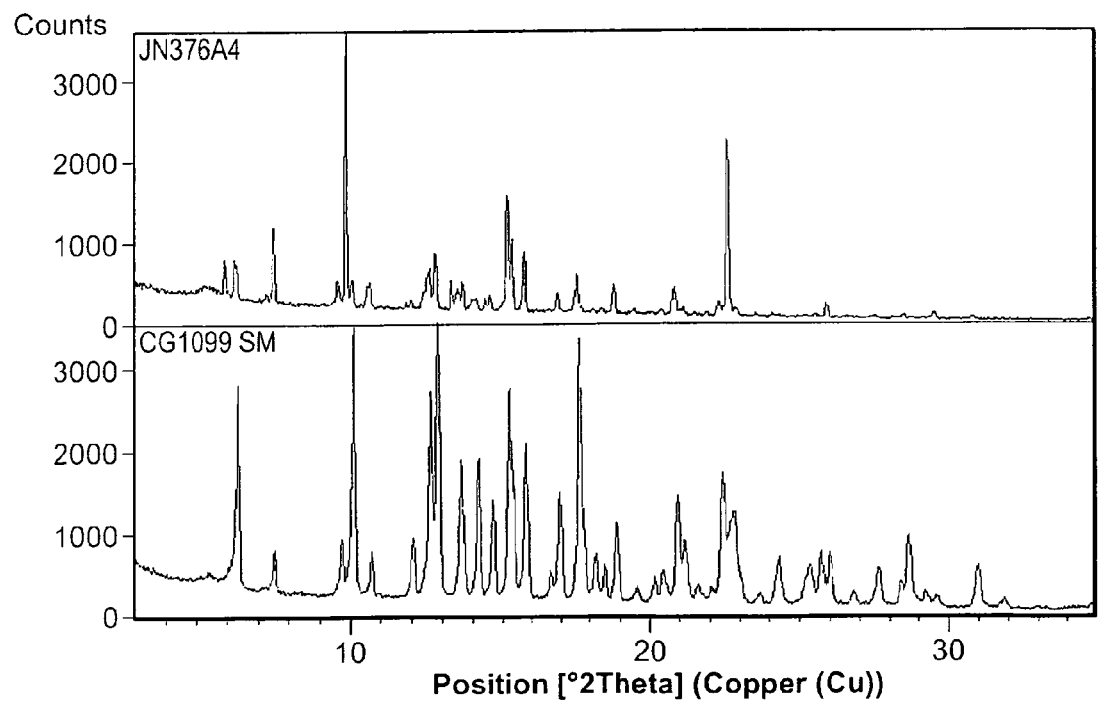
FIG. 6: XRPD comparison of RPL554 and DMSO derived saturated solution crystals (JN376A4).
Figure 7:
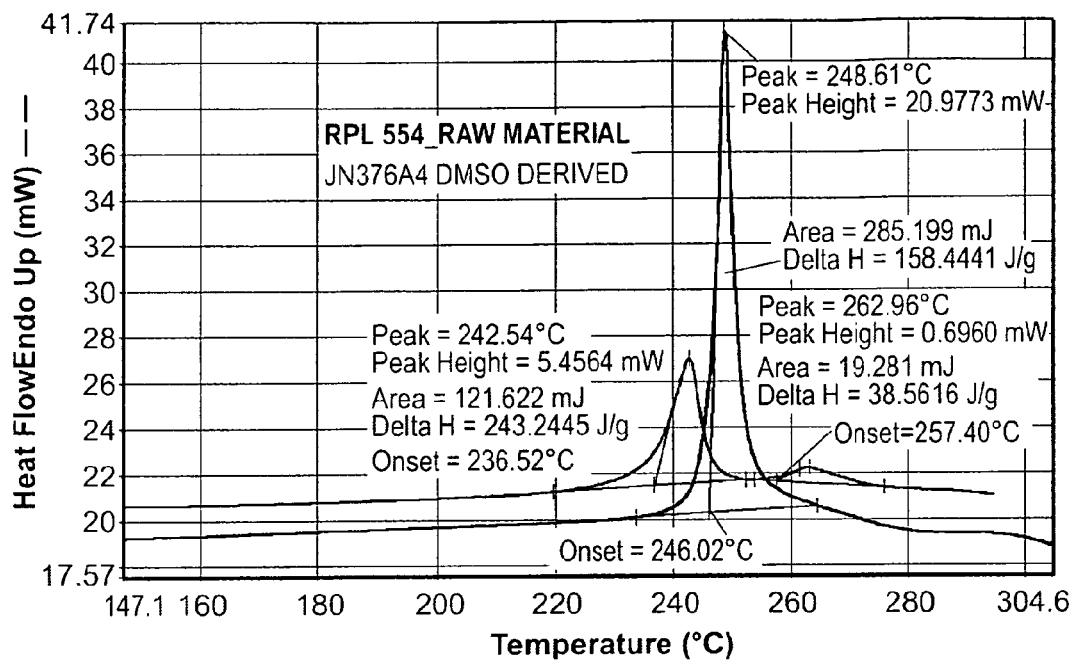
FIG. 7: DSC overlay of RPL554 input and new Form from saturated DMSO solution (JN376A4).

The results for the DMSO entry are shown below (FIGS. 6 and 7), and while the material displays some similarity to Form I, it is believed that a new polymorph is present based upon the XRPD and allowing for preferred orientation. The DSC analysis of the material gives a clearer indication of form change with a much lower onset of the main endotherm. There was insufficient material for TGA and NMR analysis. It is our understanding that this is a less stable form of RPL554.

Example 5

Slurry Maturations

24× Slurry maturations were performed in an attempt to stress the current crystalline solid into undergoing form transformation. The most effective method for such work is to utilise prolonged heat/cool cycles, as was subjected to RPL554 Form I.

Experimental (CG 1100):

Some 20 mg of material was agitated in glass tubes in approximately 30 volumes of solvent and cycled between isothermal periods (8 hours) of 20° C. and 50° C. After 4 days of cycling, the solids were filtered off and dried in vacuo at 45° C. prior to analysis by XRPD. All results were compared to the starting material, RPL554 (Form I); see Table 4.

TABLE 4

Slurry maturation experimentation for RPL554 (CG1100)

| Solvent | Grid entry | Observation | XRPD |
|---|---|---|---|
| Tetralin | A1 | Solⁿ → slow evap | Gum/oil |
| NMP | A2 | Solⁿ → slow evap | Gum/oil |
| Ethylene glycol | A3 | gummy solid | n/a |
| DMSO | A4 | powder | Form I |
| Anisole | A5 | powder | Form I |
| DMF | A6 | powder | Form I |
| Cumene | B1 | Solⁿ → slow evap | Gum/oil |
| 3-Me-1-BuOH | B2 | powder | Form I |
| n-BuOAc | B3 | powder | Form I |
| Toluene | B4 | powder | Form I |
| Dioxane | B5 | powder | Form I |
| Water | B6 | powder | Form I |
| Heptane | C1 | powder | Form I |
| n-PrOH | C2 | powder | Form I |
| IPA | C3 | powder | Form I |
| CH₃CN | C4 | powder | Form I |
| MEK | C5 | powder | Form I |
| EtOH | C6 | powder | Form I |
| EtOAc | D1 | powder | Form I |
| THF | D2 | powder | Form I |
| MeOH | D3 | powder | Form I |
| Acetone | D4 | powder | Form I |
| TBME | D5 | powder | Form I |
| DCM | D6 | powder | Form I |

Figure 8:
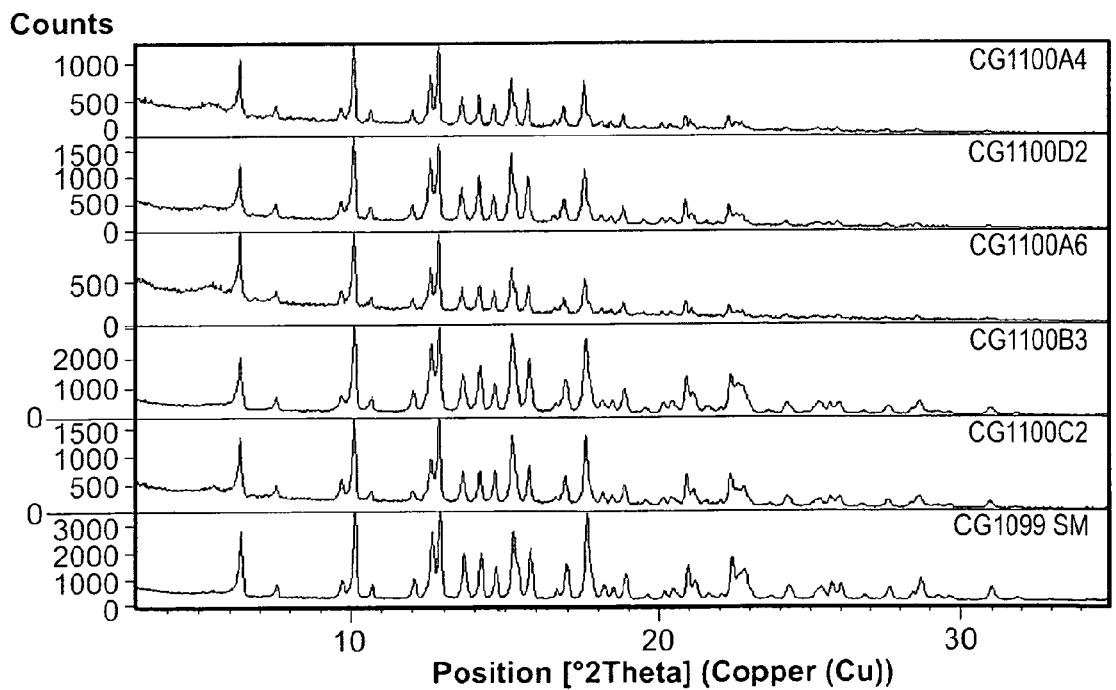
FIG. 8. Slurry maturation selected results showing Form I for all series.

All samples displayed the same XRPD profile when compared to the starting material, demonstrating that RPL554 Form I was extremely resilient to change and very likely to be the thermodynamically most stable form of the compound (FIG. 8).

Example 6

Mixed Solvent Recrystallisations

As solubility profiles can be markedly altered by the presence of mixed solvent systems and that these trends can be very difficult to predict, a series of recrystallisation using a variety of systems were planned. This was considered another suitable way to induce form change leading to the discovery of new polymorphs.

It had been noted during studies that dioxane and cumene (other than the usual DMF', DMSO and Tetralin), had shown a degree of effectiveness in dissolving RPL554. These solvents formed the basis of some initial trials that took polish filtered solutions of each solvent and RPL554 and then mixed them hot with a range of known anti-solvents of various types, maintaining a solution and then allowing a slow cool.

Experimental (PF87):

Stock solutions with 100 mg of RPL 554 were prepared by stirring the solid in 5 ml of the main solvent and leaving to heat at 50° C. to improve dissolution. An extra 1 ml (more if needed) of the co-solvent was added to improve dissolution and form the final stock mixture. Samples were left to stir at 50° C. for 30 minutes. To a pre-heated warm tube (50° C.), the stock solution was added followed by 2 ml of the anti-solvent shown in the table; the samples were left to stir and evaporate. Samples were filtered and dried overnight in a vacuum oven at 50° C. ahead of analysis by XRPD (see Table 5).

TABLE 5

Mixed solvent crystallisation of indicated stock co-solvents with anti-solvent addition (PF87)

| Stock solutions systems | Anti-Solvents | 2-Butanone | EtOAc | Heptane | IPA | MTBE |
|---|---|---|---|---|---|---|
| Dioxane/DMSO (5/1) | Form I | Form I | Form I | Form I | Form I | Form I |
| Dioxane/DCM (5/2) | Form I | Form I | Form I | Form I | Form I | Form I |
| 2MeTHF/DMSO (5/1) | Form I | Form I | Form I | Form I | Form I | Form I |
| DCM/Dioxane (5/1) | Form I | Form I | Form I | Form I | Form I | Form I |

All experiments listed in experiment PF87 returned Form I, acting as further proof as the thermodynamic stability of RPL554.

Example 7

Crystallisation Trials in Mixed Aqueous Systems

A series of mixed solvent crystallisations that had an aqueous base were investigated in experiment PF86.
Experimental (PF86):
A hot stock solution of RPL554 (Form I) in DMSO (1 ml, 15 mg·ml$^{-1}$) was added to a hot solution of solvent, mixed with water (1:1, v/v, 1 ml) as indicated in Table 6 (50° C.). The solutions were left stirring at temperature for 48 hours, cooled, filtered and then dried in the oven overnight (40° C.). Analysis by XRPD was carried out and compared to the starting material.

TABLE 6

Summary of results for aqueous mixed crystallisations (experiment PF86)

| Solvent system (+Water) | Expt | XRPD |
|---|---|---|
| Acetonitrile | PF86A | Identical to Form I |
| Dioxane | PF86B | Identical to Form I |
| Ethanol | PF86C | Identical to Form I |
| IPA | PF86D | Identical to Form I |
| MeOH | PF86E | Identical to Form I |
| THF | PF86F | Identical to Form I |

Figure 9:
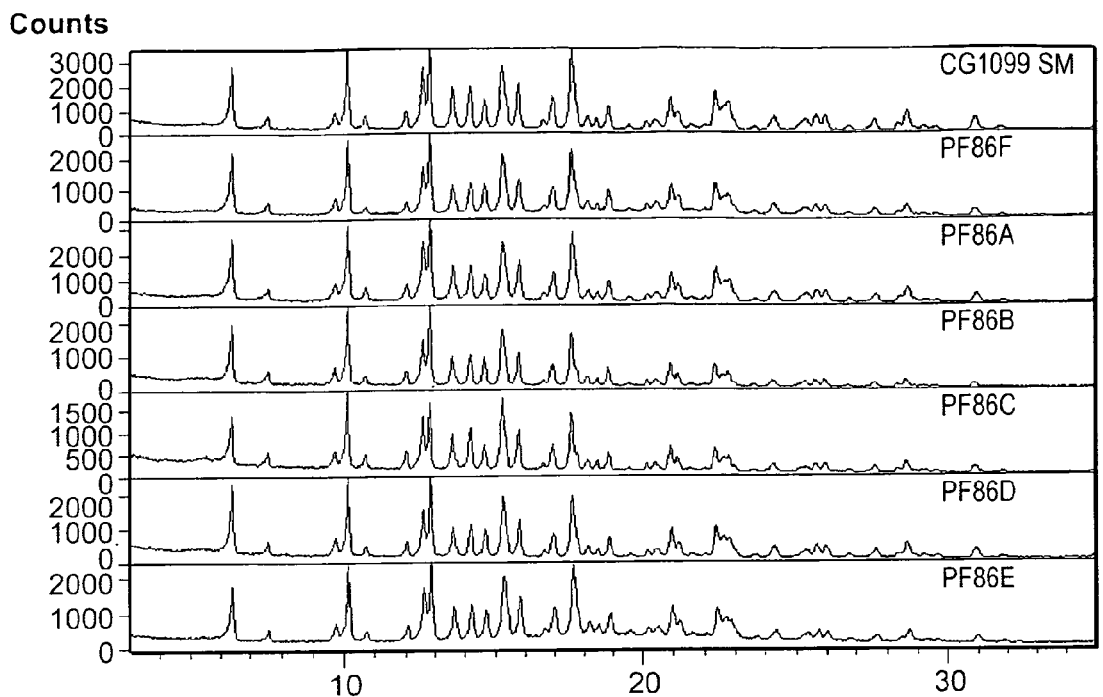
FIG. 9. XRPD profiles for aqueous mixed crystallisations (experiment PF86).

The results for this series of experiments (FIG. 9) again showed that Form I was dominant.

Example 8

Generation of amorphous material

Figure 10:
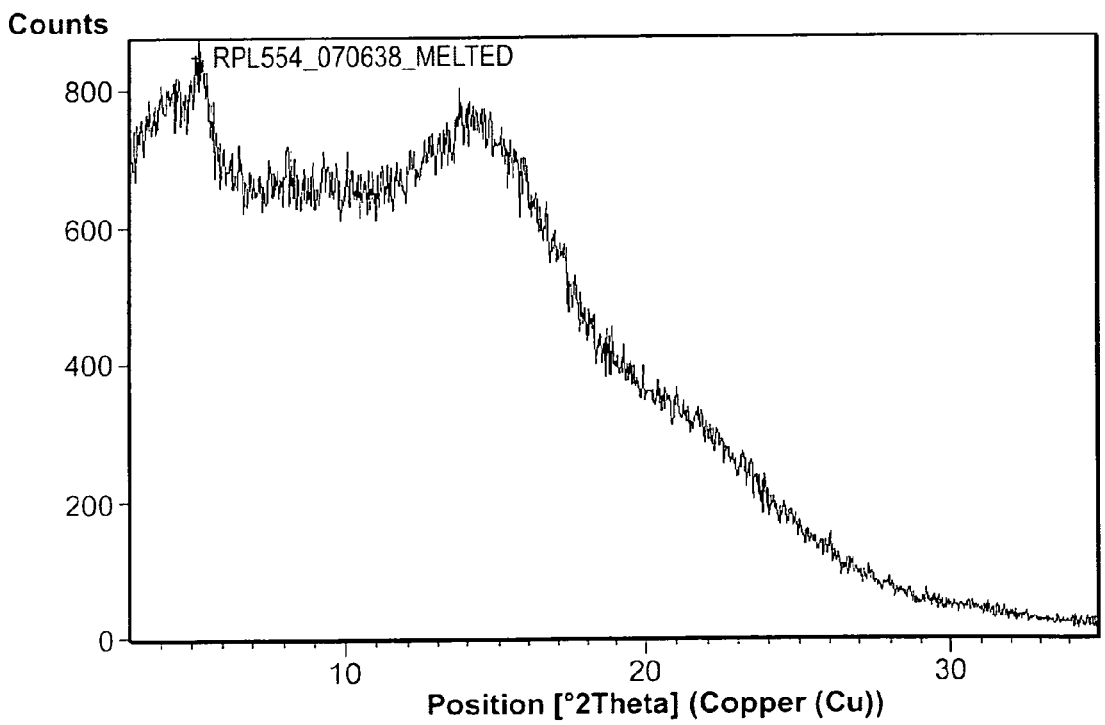
FIG. 10. Crash cooled melt of RPL554 Form I from 245° C. (performed as PF84).

As there was historical experimental proof of generating amorphous material by heating RPL554 Form I up to 245° C. and rapidly cooling the melt, a repeat of this method was performed (TGA basis) and produced the same, clear, yellow, glass like material. This specimen was subsequently analysed by XRPD and was shown to be amorphous (see FIG. 10).

Figure 11:
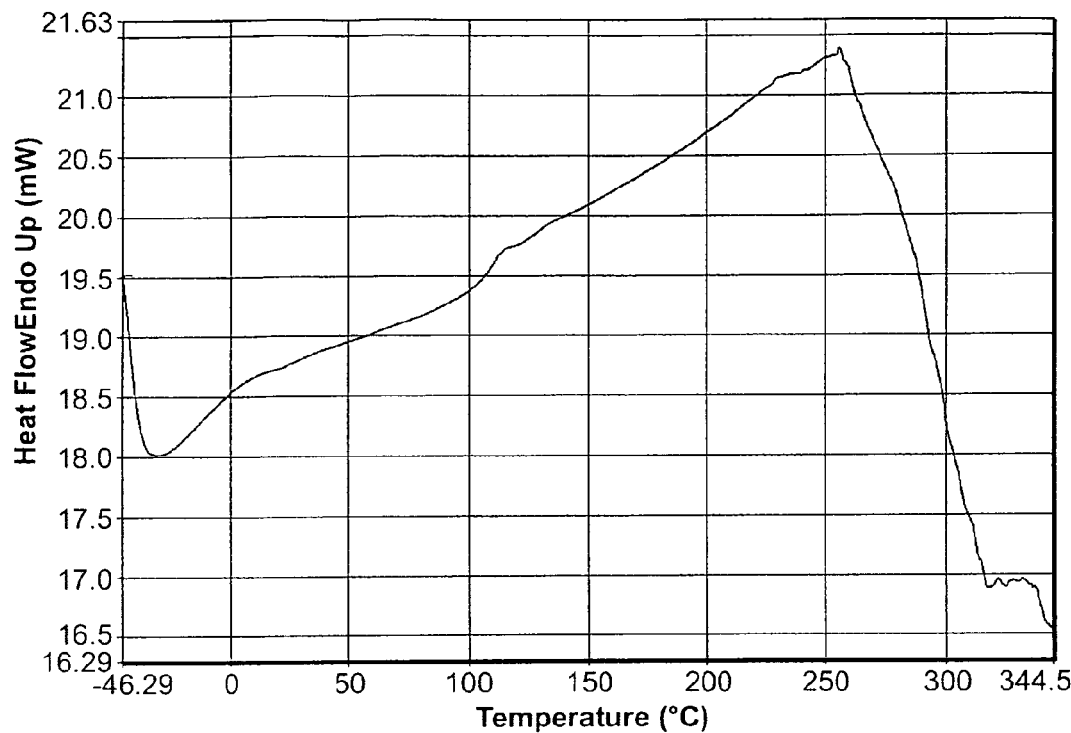
FIG. 11. DSC profile for crash cooled RPL554 (from 245° C., PF84).

This material was then run on the DSC instrument in an attempt to observe the glass transition and if possible any recrystallisations. The results are displayed in FIG. 11.

A proposed glass transition can be observed at approximately 120° C., with no formal recrystallisation observed. While this experiment was running, the sample was submitted for LC analysis, as stability at temperature was known to be a potential issue (observation of TGA). The chromatogram showed the presence of multiple peaks with only 26% of the material being the starting material, RPL554. This result indicated that either the crash cool needed to be performed with more sensitive experimental margins, or that the method was invalid. The experiment was repeated at a lower temperature (240° C.), this trying to avoid decomposition and thus return a better profile in terms of purity. LC analysis returned a similar profile of very low purity and various secondary products. It was therefore apparent that amorphous material would not be generated in this manner.

Figure 12:
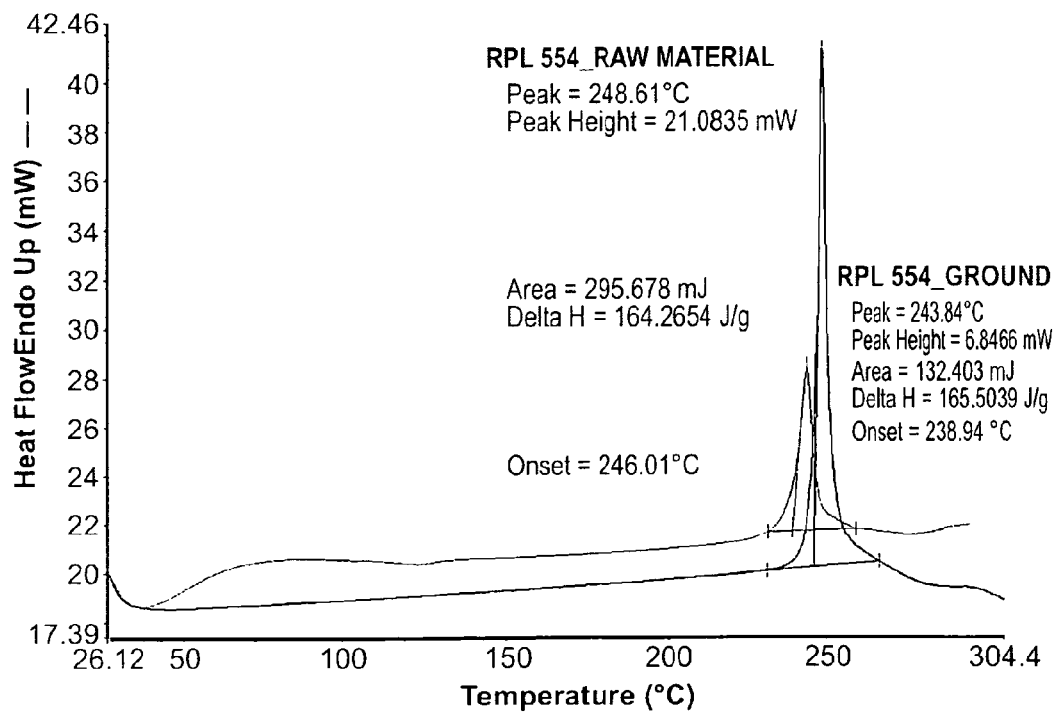
FIG. 12. DSC profile for ground RPL554 Form I.

A number of other attempts to generate the amorphous phase were then made, starting with physical manipulation (grinding, applied pressure) and then rapid evaporation of a dilute solution from solvents such as DCM and cumene. In this experiment, the ground sample (mortar and pestle), proved to be very electrostatic and failed to be transferred to the Kapton plate for XRPD analysis. The sample was, however, successfully transferred to a DSC pan; the melting point observed was lower than the reference material, indicating the possibility of form change. A repeat of this experiment would be required to further this investigation; however, the amorphous phase was not forthcoming from this approach (FIG. 12).

Figure 13:
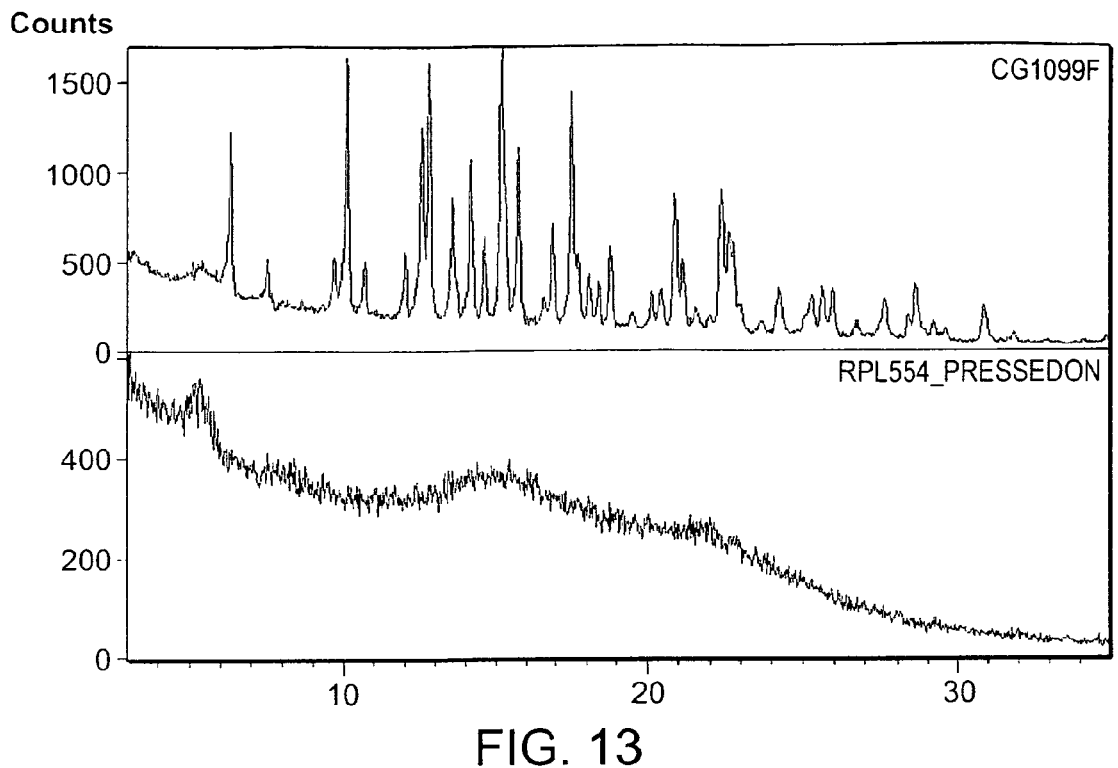
FIG. 13. XRPD comparison of compressed sample vs. original material RPL554 (CG1099 F).

Applied pressure (100 KN): 10 mg of RPL554 was left in a pressing disc system overnight, forming a fine and uniform disc with a thickness of less than 0.1 mm. The disc was gently ground and analysed by XRPD (FIG. 13).

Figure 14:
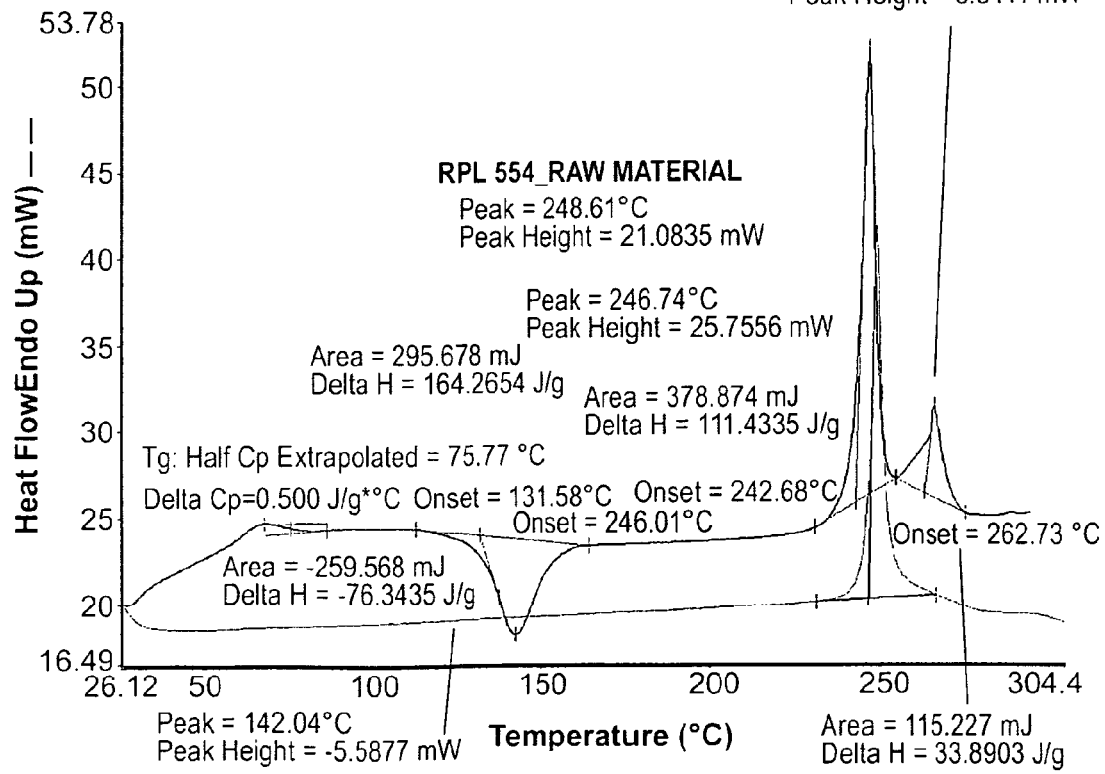
FIG. 14. DSC comparison of amorphous material via pressure vs. RPL554 DSC.

XRPD comparison of the pressurised material with the starting Form (CG1099F reference used), demonstrates that compressing the crystalline material generates an amorphous phase. Following these observations, a thermal analysis (DSC) was carried out and proved that the material was amorphous (FIG. 14).

The transition from amorphous material is shown by the Tg at 75° C., which then recrystallises at ca. 131° C. before melting at 242.6° C. and 262.7° C. consecutively. The first endotherm seems to be slightly lower than the reference material and could potentially be related to a different form (purity comparisons would be a sensible study to perform ahead of assigning a new form). The second melt could also be considered as a different crystalline entity, although it must be stressed that this is in the decomposition region for this material.

Fast solvent evaporation: A flask containing RPL554-070638 was fully dissolved in a large volume of DCM at room temperature (290 ml, 2.0 g). The solvent was then removed rapidly at temperature, keeping RPL554-070638 fully dissolved, avoiding a slow precipitation of the raw material and the presence of Form I. HPLC analysis showed a high chemical purity and proton NMR indicated a trace of residual DCM.

Figure 15:
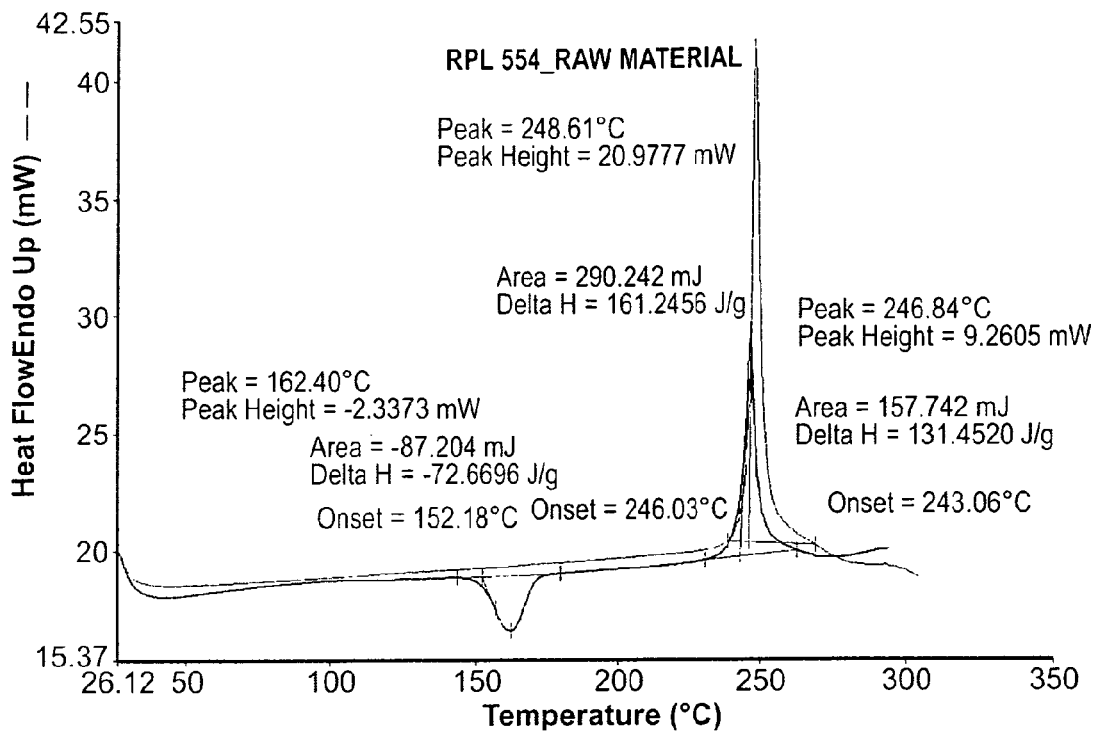
FIG. 15. DSC comparison of RPL554 and a batch of amorphous RPL554 from DCM (1N376).

XRPD of the initial batch showed an amorphous phase (JN376E,), which was confirmed by DSC (FIG. 15). The heating process induces a large exotherm, illustrating a crystallisation at 152° C., followed by an endotherm for the expected melt of Form I, albeit slightly suppressed. Note the subtle differences between this batch and the amorphous material derived from applied pressure (main difference in the temperature of the initial exotherm and profile post main melt).

Figure 16:
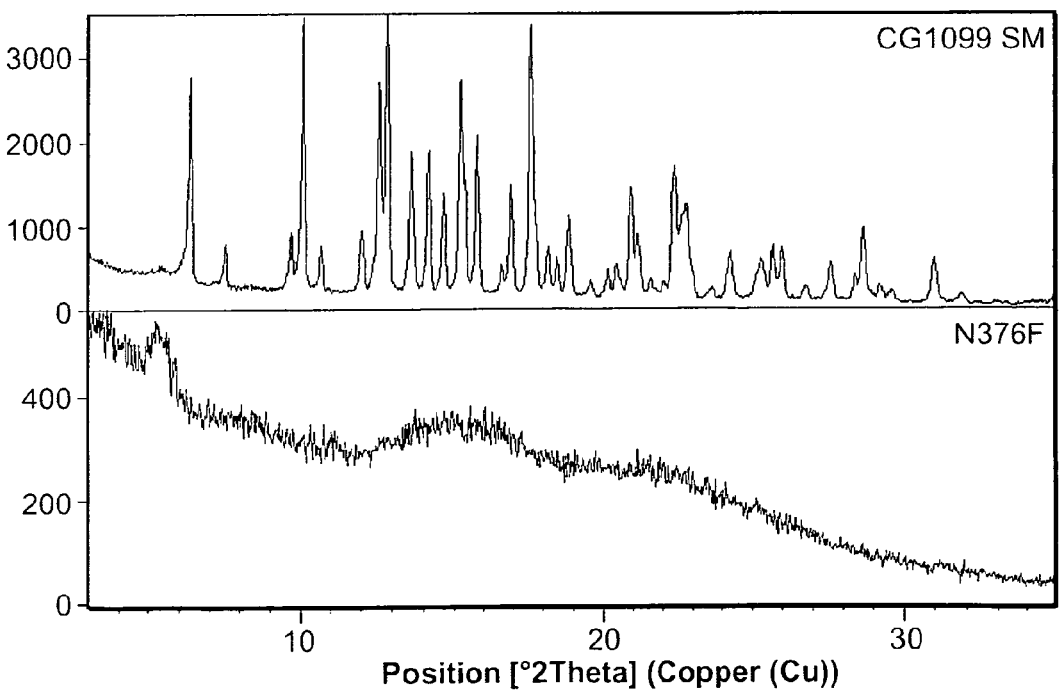
FIG. 16. XRPD analysis of RPL554 (CG1099 SM) and amorphous material (JN376F).
Figure 17:
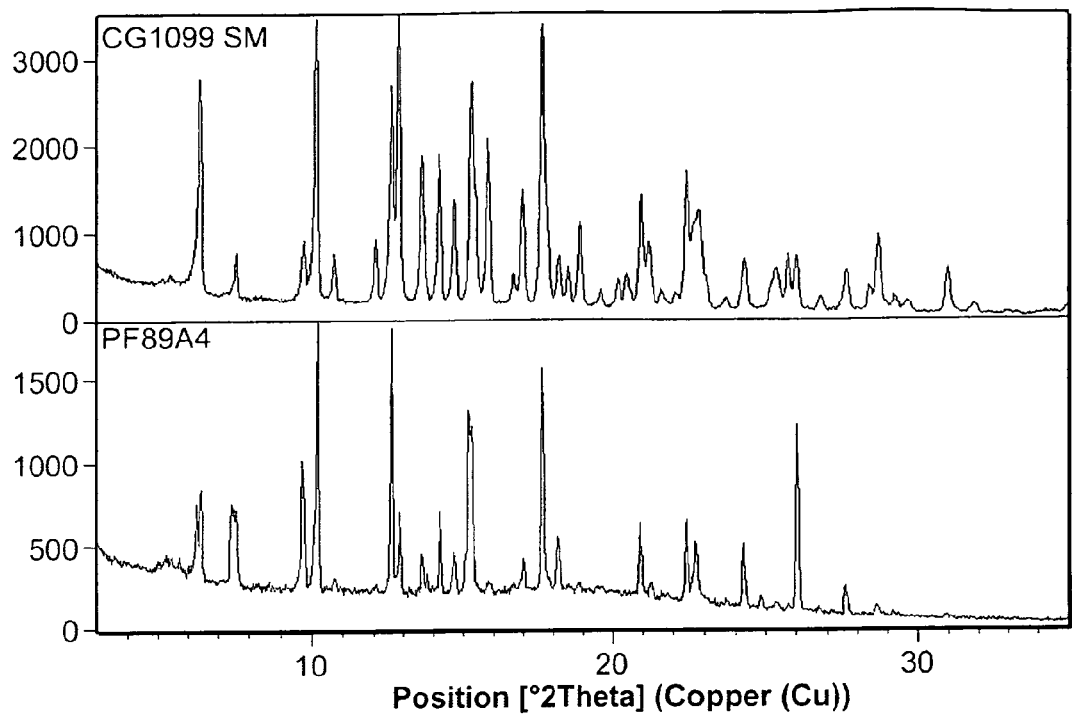
FIG. 17. XRPD Comparison for PF89A4 (DMSO) with RPL554 Form I.

Having successfully isolated a small quantity of amorphous material, the technique was scaled-up to grams of material for use in saturated solution and slurry work. The reference XRPD profile for this batch (JN376F) is shown in FIG. 16.

Example 9

Saturated Solutions with Amorphous Material

As indicated, saturated solutions are the best method of obtaining pure phases of new polymorphs. To this end, the amorphous material was taken and a study performed using saturated solutions, as in JN376, with the aim of obtaining a higher overall starting concentration.

Experimental (PF89):

24 solvents were stirred at 45° C. in the presence of 30 mg of RPL554 (JN376F) to leave an initial (more concentrated) suspension than with the crystalline phase. The suspensions were heated over a period of 4.5 hours to increase the solubility. Each tube was checked for full dissolution of the material. If solid remained, an extra 1 ml of the known solvent was added until fully dissolved. Each tube was assessed before hot filtration into pre-warmed tubes that were then left to slowly evaporate. Note that tubes were placed under nitrogen to aid evaporation for 24 hours. The results of this experiment are shown in the table below (Table 7):

TABLE 7

Saturated solution experiments (amorphous phase input, expt PF89)

| Solvent | Grid entry | Observation | XRPD |
|---|---|---|---|
| Tetralin | A1 | Oil | N/A |
| NMP | A2 | Not dry | Wet but Form I |
| Ethylene glycol | A3 | No precipitation observed | N/A |
| DMSO | A4 | Liquid + Crystals | Mixed form (measured wet) |
| Anisole | A5 | Gum/oil | N/A |
| DMF | A6 | Liquid + Crystals | Form I |
| Cumene | B1 | Liquid | Insufficient mats |
| 3-Me-1-BuOH | B2 | Crystals | Form I |
| n-BuOAc | B3 | Crystals | Form I |
| Toluene | B4 | Crystals | Form I |
| Dioxane | B5 | Crystals | Form I |
| Water | B6 | insol | N/A |
| Heptane | C1 | solid | Form I |
| n-PrOH | C2 | solid | Form I |
| IPA | C3 | solid | Form I |
| $CH_3CN$ | C4 | Extra peaks | Form I |
| MEK | C5 | Extra peaks | Form I |
| EtOH | C6 | solid | Form I |
| EtOAc | D1 | solid | Form I |
| THF | D2 | Extra peaks | Form I |
| MeOH | D3 | Split 1st peak | Form I |
| Acetone | D4 | — | Insufficient mats |
| TBME | D5 | Amorphous | N/A |
| DCM | D6 | Amorphous | N/A |

From the table it can be seen that some of the experiments dissolved an insufficient amount of material to allow for analysis, or returned either a speck of oil or amorphous powder at the bottom of the tube post drying. However, despite this, a number of experiments returned material in powder form that allowed XRPD analysis to be collected. The most successful experiments, some having shown formal crystals to be growing from the mother liquors have been harvested and only one entry showed any relevant form change (PF89A4, DMSO).

The results for the DMSO entry are shown below, and whilst the material displays some similarity to Form I, it is believed that a new polymorph is present based upon the XRPD and allowing for preferred orientation. The DSC analysis of the material gives a clearer indication of form change with a much lower onset of the main endotherm. There was insufficient material for TGA and NMR analysis. This result was scaled-up for further investigation, although it is notable that this material did not present the same, but altered profile relative to RPL554 as JN3776A4 (saturated solution from DMSO, FIGS. 6 and 7). It was considered that this would be due to relative level of solvation.

In order to aid the understanding of the analysis collected, and due to the fact that high quality modelling information had been gained from the predicted unit cell parameters (indexing experiment) for RPL554, the new phase was compared with this theoretical data.

The numerical analysis demonstrates that most of the material is form I with some peaks not being fitted. This indicated strong evidence that the sample was either a mix of two forms, one potentially a solvated product. The results have not been reported in full and were straight forward in that Form I was observed in all cases where sufficient material remained for collection, except for DMSO, where a minor change was noted in the XRPD profile.

Example 10

Automated Experiment (Expanded Anti-solvent Study)

An experiment was initiated to expand the solvent range from that used in the anti-solvent addition work and to perform such solvent mixing at temperature, instead of crash cooling via the use of anti-solvent (CG1099).

Experimental (PF85):

A defined amount of RPL554 (1.5 g) and 20 ml of DMSO was added to a tube and heated to 50° C. to improve dissolution. 200 μl of the stock solution was placed in a heated well (50° C.). 200 μl of the listed solvent (table below) was added to the well and left agitating over 72 hours ahead of isolation. Samples were then transferred onto a Kapton plate for XRPD analysis. Results were processed and compared with the starting material RPL554 (Table 8). Where XRPD was insufficient to differentiate from the starting material, thermal analysis was carried out in order to define melting points (material allowing).

TABLE 8

Automated hot mixed solvent crystallisations (PF85), detailing initial results by XRPD and DSC where possible

| Solvent | Grid entry | DSC (Onset/peak) Form I ref. = (246/248) | XRPD conclusion | Overall Conclusion (DSC/XRPD) |
|---|---|---|---|---|
| Formamide | A12 | Wet sample | Form I | Form I |
| N-Methyl-2-pyrrolidinone(NMP) | A11 | 241° C./247° C. | Poor Diffraction (probably Form I) | Form I |

TABLE 8-continued

Automated hot mixed solvent crystallisations (PF85), detailing initial results by XRPD and DSC where possible

| Solvent | Grid entry | DSC (Onset/peak) Form I ref. = (246/248) | XRPD conclusion | Overall Conclusion (DSC/XRPD) |
|---|---|---|---|---|
| Ethylene glycol | A10 | Gum | Form I | Form I |
| Dimethyl sulfoxide (DMSO) | A9 | 243° C./248° C. | Form I + Extra peaks | Form I |
| N,N-Dimethylacetamide | A8 | | Form I + Extra peaks | Form I |
| Anisole | A7 | | Form I + Extra peaks | Form I |
| N,N-Dimethylformamide | A6 | | Form I + Extra peaks | Form I |
| Cumene | A5 | Gum 240° C./246.2° C. | Different from starting material | Form II |
| 1-Pentanol | A4 | | Poor Diffraction (probably Form I) | Form I |
| Chlorobenzene | A3 | 241° C./246.7° C. | Slightly different | Form II |
| 3-Methyl-1-butanol | A2 | | Form I | Form I |
| Methylbutyl ketone = 2-Hexanone | A1 | | Form I | Form I |
| Butyl acetate | B12 | Gum | Form I | Form I |
| 2-Methoxyethanol | B11 | | Form I | Form I |
| Acetic acid | B10 | 241.6° C./247.4° C. | Strong preferred orientation | Form II |
| 1-Butanol | B9 | Gum | Wet sample but form I | Form I |
| Methylisobutyl ketone = 4 Methyl 2 pentanone | B8 | | Form I | Form I |
| isobutyl acetate | B7 | | Form I | Form I |
| Pyridine | B6 | | Form I | Form I |
| Toluene | B5 | 239.5° C./246° C. | preferred orientation (Most likely Form I) | Form II |
| 2-Methyl-1-propanol | B4 | 233° C./243° C. | preferred orientation | Form III |
| Propylacetate | B3 | | Form I + Exra peaks | Form I |
| Nitromethane | B2 | | Form I + Extra peaks | Form I |
| Dioxane | B1 | 243° C./248° C. | Uncertain due to preferred orientation | Form I |
| Methylcyclohexane | C12 | | Form I | Form I |
| Formic acid | C11 | | Form I | Form I |
| Water | C10 | 243° C./247° C. | | Form I |
| 2-Butanol | C9 | | Form I | Form I |
| Heptanes | C8 | | Form I | Form I |
| 1-Propanol | C7 | 242° C./247° C. | Form I | Form I |
| Isopropyl acetate | C6 | | | Form I |
| 1,2-Dimethoxy-ethane (glyme, DME) | C5 | 242.3° C./248° C. | | Form I |
| 2-Propanol | C4 | | Form I | Form I |
| Acetonitrile | C3 | | Form I | Form I |
| Cyclohexane | C2 | | Form I | Form I |
| Ethanol | C1 | | Form I | Form I |
| Ethyl acetate | D12 | Gum. Two endotherms, 226° C./268° C. | PO or different | 2 endos, potentially Form IV and V |
| 1,1,2-Trichloroethene | D11 | | Form I + Extra peaks | Form I |
| Hexane | D10 | 223.6° C. | Preferred orientation | Pure form IV |
| Tetrahydrofuran (THF) | D9 | Gum | Preferred Orientation for Form I | Form I |
| Methanol | D8 | 242° C./247° C. | Different or Form I (PO?) | Form I |
| Chloroform | D7 | | Form I + Extra peaks | Form I |

TABLE 8-continued

Automated hot mixed solvent crystallisations (PF85), detailing initial results by XRPD and DSC where possible

| Solvent | Grid entry | DSC (Onset/peak) Form I ref. = (246/248) | XRPD conclusion | Overall Conclusion (DSC/XRPD) |
|---|---|---|---|---|
| Methyl acetate | D6 | | Form I | Form I |
| Acetone | D5 | | Form I | Form I |
| tert-Butylmethyl ether (MTBE) | D4 | | Form I + Extra peaks | Form I |
| Ethyl formate | D3 | | Form I | Form I |
| Dichloromethane | D2 | | Form I | Form I |
| 1,2-Dichloroethene | D1 | | Form I + Extra peaks | Form I |

It can be seen from the tabulated results, especially those indicated by the DSC traces collected, that some potentially new or mixed phases were isolated from the wider anti-solvent library. While XRPD patterns may look initially different, due to peak intensities, preferred orientation effects may be present and so a more in depth analysis can be necessary (preferred orientation was considered possible due to visual observation of the transferred crystals from the automated experiment) (results not shown). Such analysis has also been presented by numerical comparison of the new XRPD patterns with the predicted Form I pattern from indexing. The idea was to gain as much quality data about the presence of a true new phase or whether the result was in fact a mixture from the initial samples.

For the parallel experiment PF85, the results provided some relatively interesting information about the ability of RPL554 to exhibit different crystalline forms. The combined analytical tools (XRPD/DSC) revealed that at least five crystalline forms potentially existed alongside RPL554 Form I, although the feeling was that these were mostly mixtures. The experiments that returned the most likely evidence of new phases and were selected for scale-up were (note that other systems may have replicated these results):

| PF85A3 | Chlorobenzene/DMSO |
| PF85A5 | Cumene/DMSO |
| PF85B4 | 1-Methyl-2-propanol/DMSO |
| PF85D10 | Hexane/DMSO |
| PF8512 | Ethyl acetate/DMSO |

Numerical Comparison of the Above 5 Forms with the Calculated RPL554 Form I Pattern The data that relates to the potential new polymorphs of RPL554 and the calculated profile of Form I (data not shown). For this study, referral is made to the unit cell parameters found while attempting to index RPL554 Form I. The algorithm in the software allows the input of unit cell parameters, in this case those related to Form I. The software then calculates a profile thus allowing the user to compare visually with the measured data. This approach aids confirmation of the existence of a new form and/or a new form coexisting with Form I (mixture). In almost all cases above, the noted result is that Form I was present and mainly mixtures have presented rather than a new, pure phase with the potential for D 0 being the exception. All of the above candidates were targeted for scale-up.

Example 11

Scale-up of the Potential New Forms

A series of scale-up experiments was initiated in order to generate more material of the new and/or mixed forms. In this way a more in detailed study could be performed and cross over slurries attempted. It should be noted that such scale-up can be non-trivial, especially where less stable forms have been induced on a small-scale (process subtleties mean that scale-up can be testing).

Experimental (PF90 and JN386):

A stock solution of RPL554 was prepared in hot DMSO. The solution was polished filtered and 1.75 ml (approx. 200 mg content) added to a volume (4 ml) of hot solvent (55° C.). Samples were left to stir and slowly evaporate over time in order to mimic the conditions that generated the potential new polymorphs. After precipitation, the samples were filtered and dried in vacuo at 40° C. before analysis by XRPD. The table below (Table 9) summarises the scale-up experiments for RPL554.

TABLE 9

Results for the scale-up of potential polymorphs showing the predominance of Form I

| Solvents (DMSO and . . . ) | Observations | XRPD |
|---|---|---|
| Ethyl Acetate (JN384A) | Precipitated as a powder, within 24 hours | Form I |
| 2-Me-1-propanol PF90 | Fine crystals | Form I |
| Acetic Acid PF90 | Gum | N/A |
| Chlorobenzene PF90 | A small portion of the wet sample was placed on XRD | Form I |
| Cumene PF90 | Very fine powder | Form I |
| DMSO PF90 | Solid formed with decent size crystals | Slightly Different XRPD (see below) |
| Hexane PF90 | The sample was left evaporating slowly with no stirring | Form I |

With the materials in hand, analysis such as TGA would be applicable to determine whether solvation is the cause of the differences in XRPD profiles (e.g. mixed phase of Form 1 and a solvate), or whether it is due to a non-solvated mixture of forms. In the case of ethyl acetate for example, it can be seen that scaling the process up has returned Form 1 and so it is most likely that the more marked differences in the original XRPD profile were due to a mixture of Form 1 and a less stable form that has converted to the most stable polymorph (the lower mp endotherm present in the DSC, not within the decomposition phase is supportive of this). The same comment is true for all the other solvents except acetic acid, which returned a gum and DMSO, which returned a mixture. In this case enough material was available to confirm the presence of Form I and a less stable form, which with time would convert to the most stable form. It should be noted that this is not identical to the less stable forms identified from DMSO in PF98A4 and JN376A4, showing that this solvent has provided a number of changes to the main form, but that upon scale-up Form I was still the major component.

Figure 18:
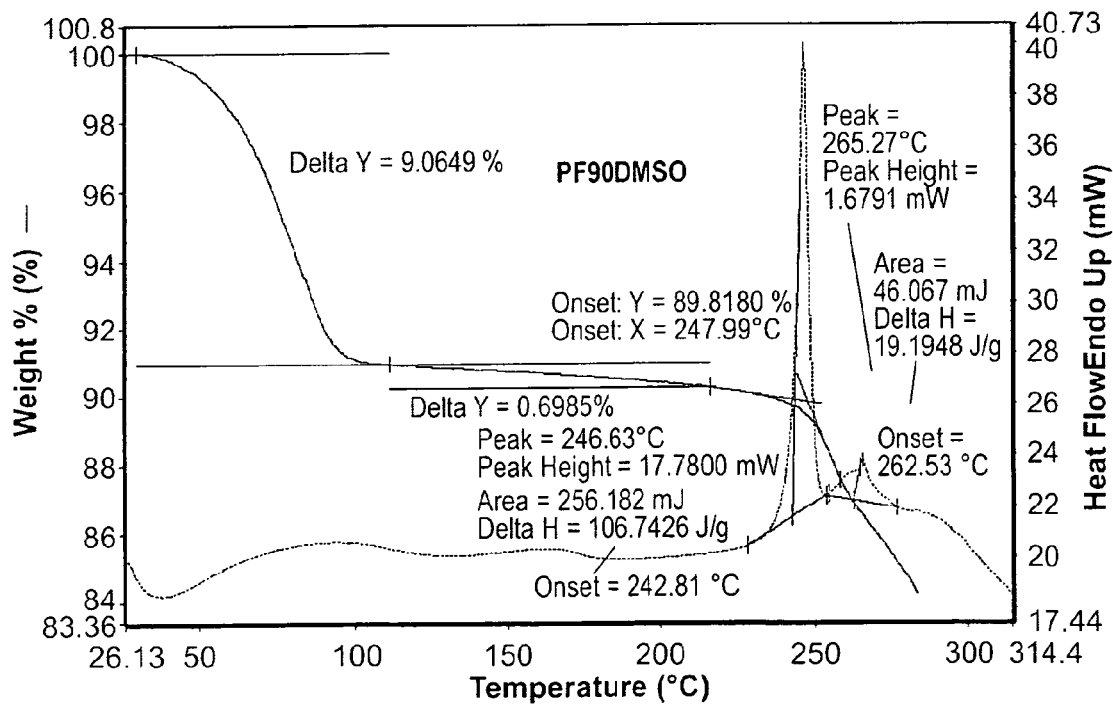
FIG. 18. Combined DSC/TGA for DMSO scale-un crystallisation PF90.
Figure 19:
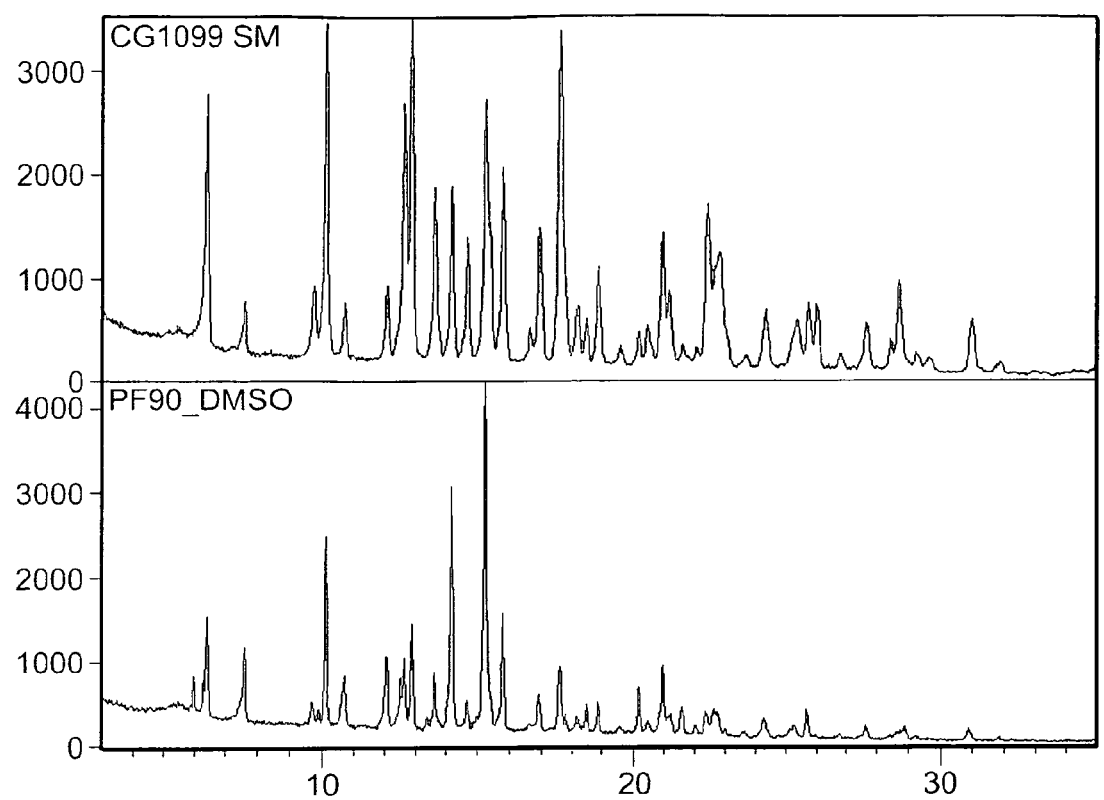
FIG. 19. XRPD comparison of RPL554 Form I with the mixed phase form DMSO (PF90).

The analysis (FIGS. 18 and 19) is related to the scale-up experiment involving DMSO.

XRPD data again clearly shows the presence of peaks that do not belong to Form I. As demonstrated in the thermal analysis, Form I is present in the majority (melting onset at 246.1° C.) while the presence of a higher melting compound (onset at 261° C.) coexists. Gravimetric analysis demonstrates the presence of free DMSO in the sample which evaporates under the nitrogen stream in the TGA when heating the sample from RT to 100° C. This cannot be related to the inclusion of the solvent in the higher melting compound. Although all the free DMSO seems to disappear upon heating, the TGA curve shows a slow but steady weight loss between 100° C. and 200° C. that may be related to 'included' DMSO, although without isolation of a pure phase, this assumptions is difficult to make. Proton NMR, as expected shows the presence of DMSO in the sample.

As a conclusion, scale up experiments for RPL554 demonstrate that Form I remains the privileged and also kinetically more favoured. It is likely that most of the mixed phases observed would ultimately convert to Form I.

Example 12

Aqueous Solubility

As amorphous material and Form I were in hand, both samples were exposed to a straight forward aqueous solubility study in purified water at 25° C. This experiment was performed as it was unknown whether crystalline or amorphous material was initially isolated in-house during a previous synthesis campaign.
Experimental:
A suspension of 20 mg of the candidate was mixed in purified water (1 ml, pH 7). The suspension was equilibrated at 25° C. for 24 hours. The suspension was then filtered into an HPLC vial and the filtrate then diluted by an appropriate factor with quantification being executed by HPLC with reference to a standard solution.
Result:

| JN376F | amorphous | 0.03 mg/ml |
| RPL554 | Form I | 0.001 mg/ml |

As expected, the amorphous phase proved, although fairly insoluble, to be more soluble than Form I under this basic test. Unfortunately, both samples were too fine to be effectively filtered and isolated for re-analysis by XRPD, although it is known that Form I results from such slurries.

Example 13

X-Ray Data: Relevant Parameters Related to RPL554 Single Crystal

Figure 20:
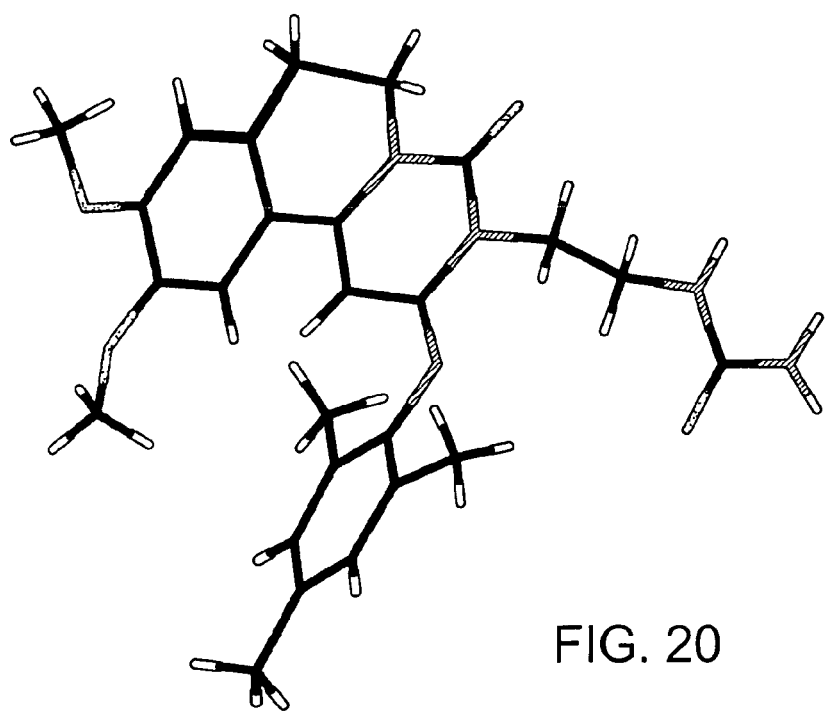
FIG. 20. Resulting conformation for RPL554 analysed by X-ray diffraction.
Figure 21:
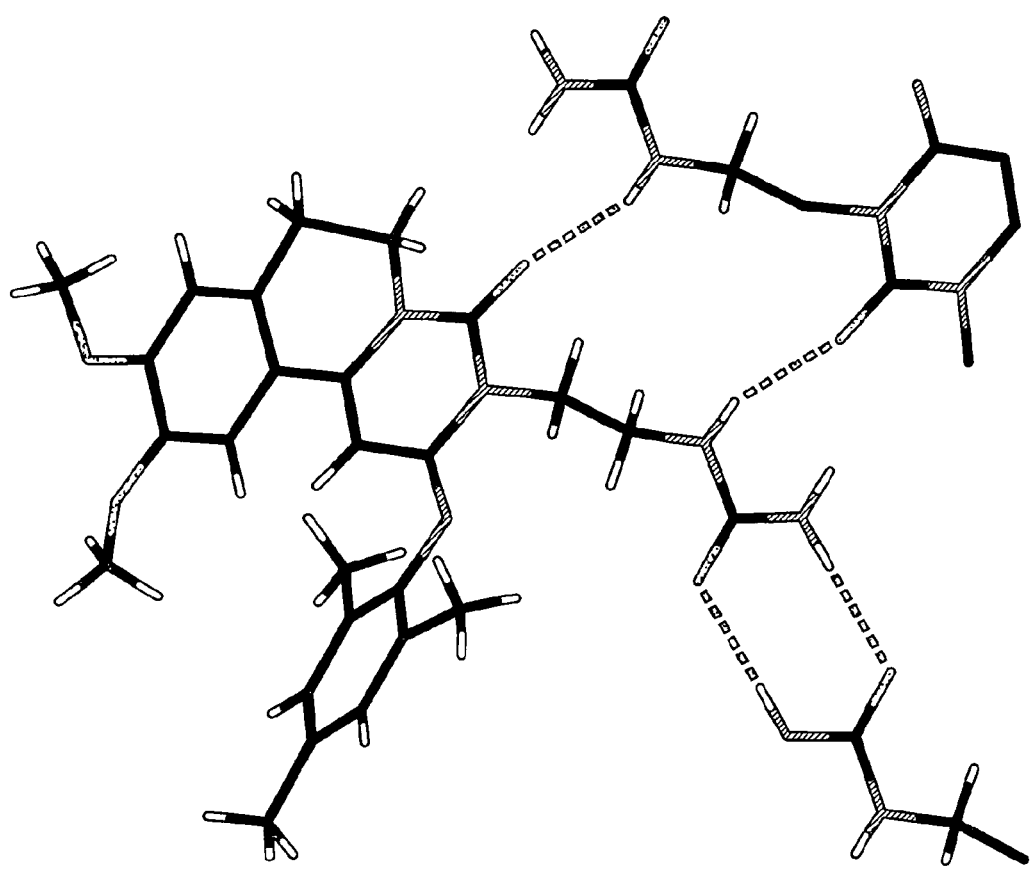
FIG. 21. Hydrogen bonding involved in RPL554 framework.
Figure 22:
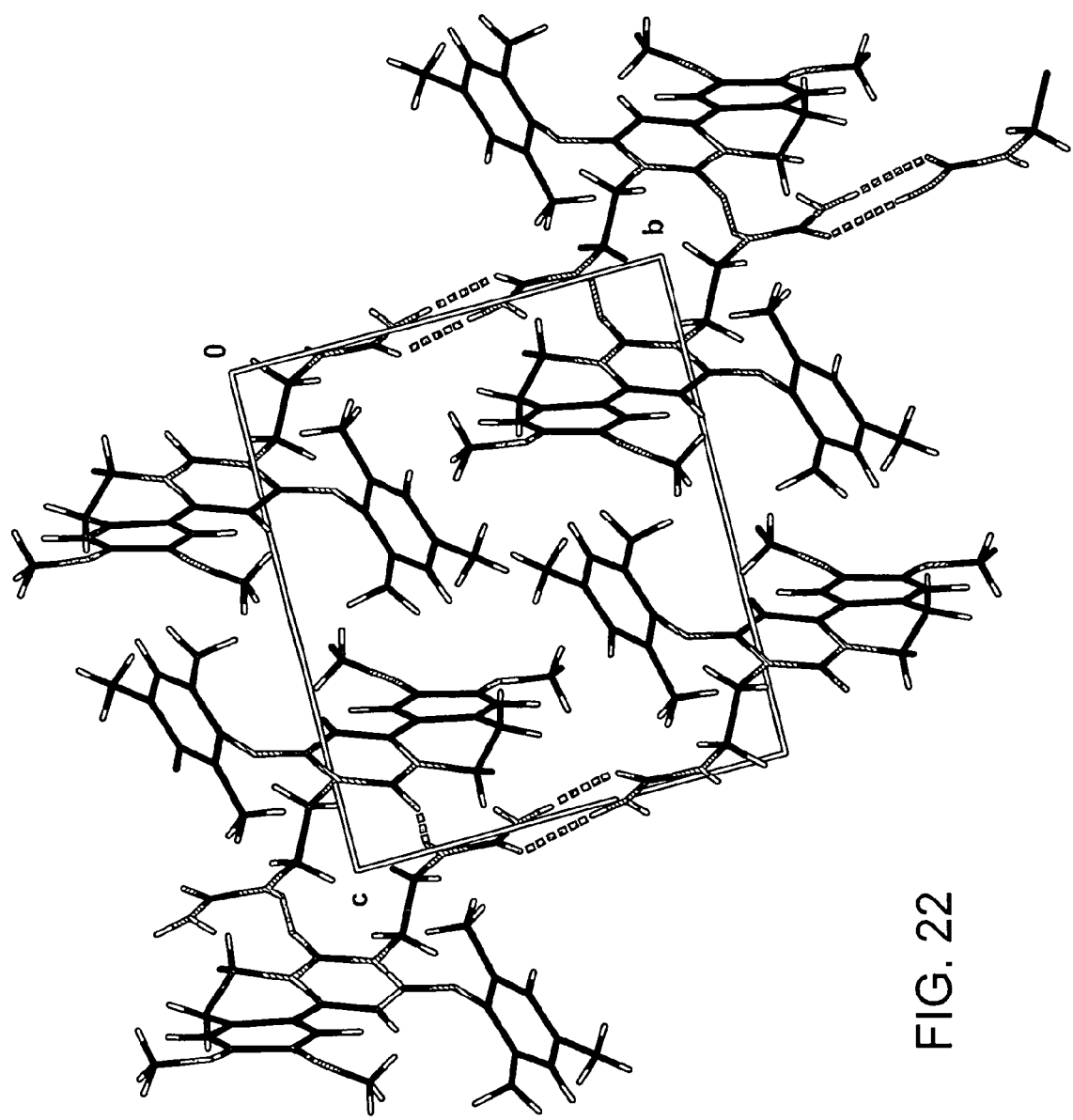
FIG. 22. Packing motif for RPL554.

X-ray data for RPL554 can be found in Tables 10-15, and FIGS. 20-22.

TABLE 10

Crystal data and structure refinement for RPL554 (onyx2010a).

| | |
|---|---|
| Identification code | onyx2010a |
| Empirical formula | C26H31N5O4 |
| Formula weight | 477.56 |
| Temperature | 123(2) K |
| Wavelength | 0.71073 Å |
| Crystal system | Triclinic |
| Space group | P-1 |
| Unit cell dimensions | a = 8.1246(4) Å   α = 91.583(4)°. |
| | b = 11.4573(5) Å   β = 90.299(4)°. |
| | c = 13.2398(6) Å   γ = 99.628(4)°. |
| Volume | 1214.56(10) Å$^3$ |
| Z | 2 |
| Density (calculated) | 1.306 Mg/m$^3$ |
| Absorption coefficient | 0.090 mm$^{-1}$ |
| F(000) | 508 |
| Crystal size | 0.32 × 0.22 × 0.08 mm$^3$ |
| Theta range for data collection | 2.86 to 30.72°. |
| Index ranges | −11 <= h <= 11, −16 <= k <= 16, −17 <= l <= 17 |
| Reflections collected | 13256 |
| Independent reflections | 6619 [R(int) = 0.0281] |
| Completeness to theta = 27.50° | 99.9% |
| Absorption correction | Semi-empirical from equivalents |
| Max. and min. transmission | 1.00000 and 0.94889 |
| Refinement method | Full-matrix least-squares on F$^2$ |
| Data/restraints/parameters | 6619/0/333 |
| Goodness-of-fit on F$^2$ | 0.854 |
| Final R indices [I > 2sigma(I)] | R1 = 0.0420, wR2 = 0.0852 |
| R indices (all data) | R1 = 0.0802, wR2 = 0.0913 |
| Largest diff. peak and hole | 0.309 and −0.240 e · Å$^{-3}$ |

TABLE 11

Atomic coordinates (×10$^4$) and equivalent isotropic displacement parameters (Å$^2$ × 10$^3$) for onyx2010a. U(eq) is defined as one third of the trace of the orthogonalized U$^{ij}$ tensor.

| | x | y | z | U(eq) |
|---|---|---|---|---|
| O(1) | 2377(1) | 8343(1) | 861(1) | 21(1) |
| O(2) | −7077(1) | 8128(1) | 3364(1) | 22(1) |
| O(3) | −7605(1) | 5925(1) | 2796(1) | 22(1) |
| O(4) | 3558(1) | 13706(1) | 485(1) | 24(1) |
| N(1) | −69(1) | 8094(1) | 1717(1) | 16(1) |
| N(2) | 1803(1) | 9907(1) | 1810(1) | 16(1) |
| N(3) | 1201(1) | 11536(1) | 2713(1) | 18(1) |
| N(4) | 4497(2) | 11982(1) | 120(1) | 21(1) |
| N(5) | 6214(2) | 13771(1) | −66(1) | 21(1) |
| C(1) | 1430(2) | 8757(1) | 1440(1) | 16(1) |
| C(2) | 742(2) | 10441(1) | 2447(1) | 16(1) |
| C(3) | −772(2) | 9687(1) | 2707(1) | 17(1) |
| C(4) | −1198(2) | 8572(1) | 2327(1) | 15(1) |
| C(5) | −2840(2) | 7838(1) | 2490(1) | 15(1) |
| C(6) | −3091(2) | 6628(1) | 2273(1) | 16(1) |
| C(7) | −1613(2) | 6080(1) | 1962(1) | 20(1) |
| C(8) | −487(2) | 6879(1) | 1271(1) | 20(1) |
| C(9) | −4174(2) | 8364(1) | 2861(1) | 17(1) |
| C(10) | −5720(2) | 7695(1) | 2993(1) | 17(1) |
| C(11) | −6002(2) | 6483(1) | 2709(1) | 17(1) |
| C(12) | −4684(2) | 5960(1) | 2371(1) | 18(1) |
| C(13) | −6739(2) | 9152(1) | 4018(1) | 26(1) |
| C(14) | −7922(2) | 4669(1) | 2626(1) | 27(1) |
| C(15) | 16(2) | 12112(1) | 3230(1) | 17(1) |
| C(16) | 318(2) | 12495(1) | 4241(1) | 20(1) |
| C(17) | −752(2) | 13173(1) | 4697(1) | 23(1) |
| C(18) | −2120(2) | 13474(1) | 4191(1) | 23(1) |

TABLE 11-continued

Atomic coordinates (×10⁴) and equivalent isotropic displacement parameters (Å² × 10³) for onyx2010a. U(eq) is defined as one third of the trace of the orthogonalized $U^{ij}$ tensor.

|  | x | y | z | U(eq) |
|---|---|---|---|---|
| C(19) | −2386(2) | 13077(1) | 3191(1) | 22(1) |
| C(20) | −1340(2) | 12405(1) | 2698(1) | 19(1) |
| C(21) | 1802(2) | 12195(1) | 4804(1) | 31(1) |
| C(22) | −3260(2) | 14224(1) | 4688(1) | 34(1) |
| C(23) | −1614(2) | 12080(1) | 1592(1) | 29(1) |
| C(24) | 3339(2) | 10637(1) | 1453(1) | 18(1) |
| C(25) | 3023(2) | 11218(1) | 464(1) | 20(1) |
| C(26) | 4689(2) | 13185(1) | 189(1) | 17(1) |

TABLE 12

Bond lengths [Å] and angles [°] for onyx2010a.

| O(1)—C(1) | 1.2296(13) |
|---|---|
| O(2)—C(10) | 1.3707(14) |
| O(2)—C(13) | 1.4268(15) |
| O(3)—C(11) | 1.3583(15) |
| O(3)—C(14) | 1.4299(16) |
| O(4)—C(26) | 1.2363(14) |
| N(1)—C(1) | 1.3803(16) |
| N(1)—C(4) | 1.3948(14) |
| N(1)—C(8) | 1.4812(16) |
| N(2)—C(1) | 1.3779(16) |
| N(2)—C(2) | 1.4084(15) |
| N(2)—C(24) | 1.4686(16) |
| N(3)—C(2) | 1.2858(16) |
| N(3)—C(15) | 1.4240(15) |
| N(4)—C(26) | 1.3610(17) |
| N(4)—C(25) | 1.4436(17) |
| N(4)—H(1N) | 0.847(14) |
| N(5)—C(26) | 1.3558(17) |
| N(5)—H(3N) | 0.897(16) |
| N(5)—H(2N) | 0.876(15) |
| C(2)—C(3) | 1.4300(18) |
| C(3)—C(4) | 1.3488(17) |
| C(3)—H(3) | 0.9500 |
| C(4)—C(5) | 1.4735(17) |
| C(5)—C(6) | 1.3896(17) |
| C(5)—C(9) | 1.4093(16) |
| C(6)—C(12) | 1.3971(18) |
| C(6)—C(7) | 1.4998(17) |
| C(7)—C(8) | 1.5121(18) |
| C(7)—H(7A) | 0.9900 |
| C(7)—H(7B) | 0.9900 |
| C(8)—H(8A) | 0.9900 |
| C(8)—H(8B) | 0.9900 |
| C(9)—C(10) | 1.3725(18) |
| C(9)—H(9) | 0.9500 |
| C(10)—C(11) | 1.4099(18) |
| C(11)—C(12) | 1.3826(17) |
| C(12)—H(12) | 0.9500 |
| C(13)—H(13A) | 0.9800 |
| C(13)—H(13B) | 0.9800 |
| C(13)—H(13C) | 0.9800 |
| C(14)—H(14A) | 0.9800 |
| C(14)—H(14B) | 0.9800 |
| C(14)—H(14C) | 0.9800 |
| C(15)—C(20) | 1.3972(18) |
| C(15)—C(16) | 1.4038(17) |
| C(16)—C(17) | 1.3884(17) |
| C(16)—C(21) | 1.5074(19) |
| C(17)—C(18) | 1.3923(19) |
| C(17)—H(17) | 0.9500 |
| C(18)—C(19) | 1.3918(18) |
| C(18)—C(22) | 1.5072(17) |
| C(19)—C(20) | 1.3914(17) |
| C(19)—H(19) | 0.9500 |
| C(20)—C(23) | 1.5068(18) |
| C(21)—H(21A) | 0.9800 |
| C(21)—H(21B) | 0.9800 |
| C(21)—H(21C) | 0.9800 |

TABLE 12-continued

Bond lengths [Å] and angles [°] for onyx2010a.

| C(22)—H(22A) | 0.9800 |
|---|---|
| C(22)—H(22B) | 0.9800 |
| C(22)—H(22C) | 0.9800 |
| C(23)—H(23A) | 0.9800 |
| C(23)—H(23B) | 0.9800 |
| C(23)—H(23C) | 0.9800 |
| C(24)—C(25) | 1.5258(18) |
| C(24)—H(24A) | 0.9900 |
| C(24)—H(24B) | 0.9900 |
| C(25)—H(25A) | 0.9900 |
| C(25)—H(25B) | 0.9900 |
| C(10)—O(2)—C(13) | 116.55(10) |
| C(11)—O(3)—C(14) | 117.16(10) |
| C(1)—N(1)—C(4) | 121.65(11) |
| C(1)—N(1)—C(8) | 116.95(10) |
| C(4)—N(1)—C(8) | 121.24(11) |
| C(1)—N(2)—C(2) | 123.78(11) |
| C(1)—N(2)—C(24) | 117.51(10) |
| C(2)—N(2)—C(24) | 118.54(11) |
| C(2)—N(3)—C(15) | 117.37(11) |
| C(26)—N(4)—C(25) | 122.90(11) |
| C(26)—N(4)—H(1N) | 118.4(11) |
| C(25)—N(4)—H(1N) | 118.7(10) |
| C(26)—N(5)—H(3N) | 116.1(10) |
| C(26)—N(5)—H(2N) | 118.0(10) |
| H(3N)—N(5)—H(2N) | 117.6(14) |
| O(1)—C(1)—N(2) | 121.24(12) |
| O(1)—C(1)—N(1) | 121.00(12) |
| N(2)—C(1)—N(1) | 117.73(10) |
| N(3)—C(2)—N(2) | 118.03(12) |
| N(3)—C(2)—C(3) | 127.18(11) |
| N(2)—C(2)—C(3) | 114.78(11) |
| C(4)—C(3)—C(2) | 122.70(11) |
| C(4)—C(3)—H(3) | 118.7 |
| C(2)—C(3)—H(3) | 118.7 |
| C(3)—C(4)—N(1) | 119.19(12) |
| C(3)—C(4)—C(5) | 123.14(11) |
| N(1)—C(4)—C(5) | 117.61(11) |
| C(6)—C(5)—C(9) | 119.51(12) |
| C(6)—C(5)—C(4) | 120.45(11) |
| C(9)—C(5)—C(4) | 120.04(11) |
| C(5)—C(6)—C(12) | 119.59(11) |
| C(5)—C(6)—C(7) | 118.11(12) |
| C(12)—C(6)—C(7) | 122.29(12) |
| C(6)—C(7)—C(8) | 111.05(11) |
| C(6)—C(7)—H(7A) | 109.4 |
| C(8)—C(7)—H(7A) | 109.4 |
| C(6)—C(7)—H(7B) | 109.4 |
| C(8)—C(7)—H(7B) | 109.4 |
| H(7A)—C(7)—H(7B) | 108.0 |
| N(1)—C(8)—C(7) | 110.91(10) |
| N(1)—C(8)—H(8A) | 109.5 |
| C(7)—C(8)—H(8A) | 109.5 |
| N(1)—C(8)—H(8B) | 109.5 |
| C(7)—C(8)—H(8B) | 109.5 |
| H(8A)—C(8)—H(8B) | 108.0 |
| C(10)—C(9)—C(5) | 120.58(12) |
| C(10)—C(9)—H(9) | 119.7 |
| C(5)—C(9)—H(9) | 119.7 |
| O(2)—C(10)—C(9) | 124.53(12) |
| O(2)—C(10)—C(11) | 115.61(12) |
| C(9)—C(10)—C(11) | 119.83(11) |
| O(3)—C(11)—C(12) | 125.46(12) |
| O(3)—C(11)—C(10) | 115.06(11) |
| C(12)—C(11)—C(10) | 119.48(12) |
| C(11)—C(12)—C(6) | 120.80(12) |
| C(11)—C(12)—H(12) | 119.6 |
| C(6)—C(12)—H(12) | 119.6 |
| O(2)—C(13)—H(13A) | 109.5 |
| O(2)—C(13)—H(13B) | 109.5 |
| H(13A)—C(13)—H(13B) | 109.5 |
| O(2)—C(13)—H(13C) | 109.5 |
| H(13A)—C(13)—H(13C) | 109.5 |
| H(13B)—C(13)—H(13C) | 109.5 |
| O(3)—C(14)—H(14A) | 109.5 |
| O(3)—C(14)—H(14B) | 109.5 |
| H(14A)—C(14)—H(14B) | 109.5 |
| O(3)—C(14)—H(14C) | 109.5 |

TABLE 12-continued

Bond lengths [Å] and angles [°] for onyx2010a.

| | |
|---|---|
| H(14A)—C(14)—H(14C) | 109.5 |
| H(14B)—C(14)—H(14C) | 109.5 |
| C(20)—C(15)—C(16) | 120.45(11) |
| C(20)—C(15)—N(3) | 119.62(11) |
| C(16)—C(15)—N(3) | 119.56(12) |
| C(17)—C(16)—C(15) | 118.75(12) |
| C(17)—C(16)—C(21) | 121.09(12) |
| C(15)—C(16)—C(21) | 120.15(11) |
| C(16)—C(17)—C(18) | 122.27(12) |
| C(16)—C(17)—H(17) | 118.9 |
| C(18)—C(17)—H(17) | 118.9 |
| C(19)—C(18)—C(17) | 117.49(12) |
| C(19)—C(18)—C(22) | 120.62(13) |
| C(17)—C(18)—C(22) | 121.87(12) |
| C(20)—C(19)—C(18) | 122.35(13) |
| C(20)—C(19)—H(19) | 118.8 |
| C(18)—C(19)—H(19) | 118.8 |
| C(19)—C(20)—C(15) | 118.69(12) |
| C(19)—C(20)—C(23) | 119.92(12) |
| C(15)—C(20)—C(23) | 121.26(11) |
| C(16)—C(21)—H(21A) | 109.5 |
| C(16)—C(21)—H(21B) | 109.5 |
| H(21A)—C(21)—H(21B) | 109.5 |
| C(16)—C(21)—H(21C) | 109.5 |
| H(21A)—C(21)—H(21C) | 109.5 |
| H(21B)—C(21)—H(21C) | 109.5 |
| C(18)—C(22)—H(22A) | 109.5 |
| C(18)—C(22)—H(22B) | 109.5 |
| H(22A)—C(22)—H(22B) | 109.5 |
| C(18)—C(22)—H(22C) | 109.5 |
| H(22A)—C(22)—H(22C) | 109.5 |
| H(22B)—C(22)—H(22C) | 109.5 |
| C(20)—C(23)—H(23A) | 109.5 |
| C(20)—C(23)—H(23B) | 109.5 |
| H(23A)—C(23)—H(23B) | 109.5 |
| C(20)—C(23)—H(23C) | 109.5 |
| H(23A)—C(23)—H(23C) | 109.5 |
| H(23B)—C(23)—H(23C) | 109.5 |
| N(2)—C(24)—C(25) | 110.92(11) |
| N(2)—C(24)—H(24A) | 109.5 |
| C(25)—C(24)—H(24A) | 109.5 |
| N(2)—C(24)—H(24B) | 109.5 |
| C(25)—C(24)—H(24B) | 109.5 |
| H(24A)—C(24)—H(24B) | 108.0 |
| N(4)—C(25)—C(24) | 111.97(11) |
| N(4)—C(25)—H(25A) | 109.2 |
| C(24)—C(25)—H(25A) | 109.2 |
| N(4)—C(25)—H(25B) | 109.2 |
| C(24)—C(25)—H(25B) | 109.2 |
| H(25A)—C(25)—H(25B) | 107.9 |
| O(4)—C(26)—N(5) | 122.27(13) |
| O(4)—C(26)—N(4) | 122.15(13) |
| N(5)—C(26)—N(4) | 115.55(12) |

TABLE 13

Anisotropic displacement parameters (Å$^2$ × 10$^3$) for onyx2010a. The anisotropic displacement factor exponent takes the form: $-2\pi^2[h^2 a^{*2} U^{11} + \ldots + 2 h k a^* b^* U^{12}]$

| | U$^{11}$ | U$^{22}$ | U$^{33}$ | U$^{23}$ | U$^{13}$ | U$^{12}$ |
|---|---|---|---|---|---|---|
| O(1) | 19(1) | 20(1) | 24(1) | −1(1) | 6(1) | 4(1) |
| O(2) | 16(1) | 20(1) | 28(1) | −4(1) | 4(1) | 3(1) |
| O(3) | 16(1) | 16(1) | 32(1) | −1(1) | 2(1) | −2(1) |
| O(4) | 23(1) | 20(1) | 30(1) | 1(1) | 8(1) | 7(1) |
| N(1) | 15(1) | 14(1) | 19(1) | −1(1) | 2(1) | 2(1) |
| N(2) | 14(1) | 14(1) | 19(1) | 1(1) | 4(1) | 0(1) |
| N(3) | 17(1) | 16(1) | 19(1) | −1(1) | 1(1) | 1(1) |
| N(4) | 20(1) | 16(1) | 28(1) | 3(1) | 10(1) | 3(1) |
| N(5) | 20(1) | 15(1) | 28(1) | 3(1) | 6(1) | 2(1) |
| C(1) | 16(1) | 16(1) | 17(1) | 2(1) | 0(1) | 3(1) |
| C(2) | 16(1) | 16(1) | 16(1) | 2(1) | 0(1) | 3(1) |
| C(3) | 15(1) | 16(1) | 19(1) | 0(1) | 3(1) | 2(1) |
| C(4) | 14(1) | 16(1) | 16(1) | 3(1) | 1(1) | 3(1) |

TABLE 13-continued

Anisotropic displacement parameters (Å$^2$ × 10$^3$) for onyx2010a. The anisotropic displacement factor exponent takes the form: $-2\pi^2[h^2 a^{*2} U^{11} + \ldots + 2 h k a^* b^* U^{12}]$

| | U$^{11}$ | U$^{22}$ | U$^{33}$ | U$^{23}$ | U$^{13}$ | U$^{12}$ |
|---|---|---|---|---|---|---|
| C(5) | 15(1) | 15(1) | 14(1) | 1(1) | −1(1) | 1(1) |
| C(6) | 16(1) | 15(1) | 17(1) | 1(1) | 0(1) | 2(1) |
| C(7) | 19(1) | 14(1) | 27(1) | −1(1) | 1(1) | 2(1) |
| C(8) | 19(1) | 14(1) | 25(1) | −4(1) | 3(1) | 1(1) |
| C(9) | 18(1) | 14(1) | 19(1) | 0(1) | 1(1) | 1(1) |
| C(10) | 17(1) | 19(1) | 16(1) | 2(1) | 1(1) | 5(1) |
| C(11) | 14(1) | 18(1) | 19(1) | 3(1) | −1(1) | −1(1) |
| C(12) | 20(1) | 13(1) | 20(1) | 0(1) | 0(1) | 0(1) |
| C(13) | 24(1) | 24(1) | 32(1) | −6(1) | 4(1) | 6(1) |
| C(14) | 22(1) | 17(1) | 39(1) | −1(1) | 7(1) | −5(1) |
| C(15) | 16(1) | 12(1) | 21(1) | 0(1) | 3(1) | −2(1) |
| C(16) | 23(1) | 16(1) | 21(1) | 2(1) | 1(1) | 1(1) |
| C(17) | 31(1) | 21(1) | 17(1) | 0(1) | 3(1) | 3(1) |
| C(18) | 26(1) | 19(1) | 24(1) | 2(1) | 8(1) | 4(1) |
| C(19) | 20(1) | 20(1) | 26(1) | 3(1) | 0(1) | 3(1) |
| C(20) | 20(1) | 14(1) | 21(1) | 0(1) | 0(1) | −1(1) |
| C(21) | 37(1) | 34(1) | 22(1) | −3(1) | −7(1) | 11(1) |
| C(22) | 38(1) | 38(1) | 30(1) | −2(1) | 7(1) | 16(1) |
| C(23) | 33(1) | 34(1) | 23(1) | −4(1) | −7(1) | 13(1) |
| C(24) | 13(1) | 16(1) | 23(1) | 1(1) | 3(1) | 0(1) |
| C(25) | 17(1) | 18(1) | 24(1) | 3(1) | 3(1) | 0(1) |
| C(26) | 20(1) | 17(1) | 15(1) | 1(1) | 1(1) | 2(1) |

TABLE 14

Hydrogen coordinates (×10$^4$) and isotropic displacement parameters (Å$^2$ × 10$^3$) for onyx2010a.

| | x | y | z | U(eq) |
|---|---|---|---|---|
| H(3) | −1508 | 9983 | 3166 | 20 |
| H(7A) | −2003 | 5309 | 1609 | 24 |
| H(7B) | −974 | 5932 | 2570 | 24 |
| H(8A) | 552 | 6554 | 1154 | 24 |
| H(8B) | −1053 | 6906 | 610 | 24 |
| H(9) | −4000 | 9189 | 3022 | 20 |
| H(12) | −4863 | 5137 | 2202 | 21 |
| H(13A) | −5908 | 9037 | 4528 | 40 |
| H(13B) | −7771 | 9279 | 4352 | 40 |
| H(13C) | −6305 | 9845 | 3621 | 40 |
| H(14A) | −7656 | 4481 | 1925 | 40 |
| H(14B) | −9101 | 4366 | 2750 | 40 |
| H(14C) | −7224 | 4300 | 3085 | 40 |
| H(17) | −542 | 13440 | 5379 | 28 |
| H(19) | −3315 | 13270 | 2832 | 26 |
| H(21A) | 1975 | 12671 | 5434 | 46 |
| H(21B) | 2798 | 12366 | 4385 | 46 |
| H(21C) | 1596 | 11352 | 4961 | 46 |
| H(22A) | −4074 | 13725 | 5103 | 51 |
| H(22B) | −3849 | 14592 | 4168 | 51 |
| H(22C) | −2599 | 14843 | 5117 | 51 |
| H(23A) | −2496 | 12476 | 1324 | 44 |
| H(23B) | −1945 | 11221 | 1508 | 44 |
| H(23C) | −577 | 12334 | 1225 | 44 |
| H(24A) | 4208 | 10135 | 1350 | 21 |
| H(24B) | 3754 | 11257 | 1972 | 21 |
| H(25A) | 2653 | 10595 | −60 | 24 |
| H(25B) | 2114 | 11687 | 560 | 24 |
| H(1N) | 5292(18) | 11670(13) | −118(11) | 31(4) |
| H(3N) | 6273(19) | 14542(14) | −193(11) | 31(4) |
| H(2N) | 6881(19) | 13378(14) | −400(12) | 36(5) |

TABLE 15

Torsion angles [°] for onyx2010a.

| | |
|---|---|
| C(2)—N(2)—C(1)—O(1) | 177.74(12) |
| C(24)—N(2)—C(1)—O(1) | 2.58(17) |
| C(2)—N(2)—C(1)—N(1) | −0.33(17) |

TABLE 15-continued

Torsion angles [°] for onyx2010a.

| | |
|---|---|
| C(24)—N(2)—C(1)—N(1) | -175.49(11) |
| C(4)—N(1)—C(1)—O(1) | -176.36(11) |
| C(8)—N(1)—C(1)—O(1) | -1.08(18) |
| C(4)—N(1)—C(1)—N(2) | 1.72(17) |
| C(8)—N(1)—C(1)—N(2) | 177.00(11) |
| C(15)—N(3)—C(2)—N(2) | 170.96(11) |
| C(15)—N(3)—C(2)—C(3) | -7.54(19) |
| C(1)—N(2)—C(2)—N(3) | -177.51(12) |
| C(24)—N(2)—C(2)—N(3) | -2.40(17) |
| C(1)—N(2)—C(2)—C(3) | 1.18(17) |
| C(24)—N(2)—C(2)—C(3) | 176.30(11) |
| N(3)—C(2)—C(3)—C(4) | 174.92(13) |
| N(2)—C(2)—C(3)—C(4) | -3.63(18) |
| C(2)—C(3)—C(4)—N(1) | 5.10(19) |
| C(2)—C(3)—C(4)—C(5) | -172.25(12) |
| C(1)—N(1)—C(4)—C(3) | -4.08(18) |
| C(8)—N(1)—C(4)—C(3) | -179.16(12) |
| C(1)—N(1)—C(4)—C(5) | 173.41(11) |
| C(8)—N(1)—C(4)—C(5) | -1.67(17) |
| C(3)—C(4)—C(5)—C(6) | -166.10(12) |
| N(1)—C(4)—C(5)—C(6) | 16.51(17) |
| C(3)—C(4)—C(5)—C(9) | 14.28(19) |
| N(1)—C(4)—C(5)—C(9) | -163.11(11) |
| C(9)—C(5)—C(6)—C(12) | 3.69(18) |
| C(4)—C(5)—C(6)—C(12) | -175.93(11) |
| C(9)—C(5)—C(6)—C(7) | -174.98(11) |
| C(4)—C(5)—C(6)—C(7) | 5.40(18) |
| C(5)—C(6)—C(7)—C(8) | -39.51(16) |
| C(12)—C(6)—C(7)—C(8) | 141.86(13) |
| C(1)—N(1)—C(8)—C(7) | 152.41(11) |
| C(4)—N(1)—C(8)—C(7) | -32.29(16) |
| C(6)—C(7)—C(8)—N(1) | 51.19(15) |
| C(6)—C(5)—C(9)—C(10) | -1.21(19) |
| C(4)—C(5)—C(9)—C(10) | 178.41(12) |
| C(13)—O(2)—C(10)—C(9) | -26.55(18) |
| C(13)—O(2)—C(10)—C(11) | 155.32(12) |
| C(5)—C(9)—C(10)—O(2) | 178.92(11) |
| C(5)—C(9)—C(10)—C(11) | -3.02(19) |
| C(14)—O(3)—C(11)—C(12) | 7.02(18) |
| C(14)—O(3)—C(11)—C(10) | -173.21(11) |
| O(2)—C(10)—C(11)—O(3) | 3.21(16) |
| C(9)—C(10)—C(11)—O(3) | -175.02(11) |
| O(2)—C(10)—C(11)—C(12) | -177.01(11) |
| C(9)—C(10)—C(11)—C(12) | 4.76(19) |
| O(3)—C(11)—C(12)—C(6) | 177.47(12) |
| C(10)—C(11)—C(12)—C(6) | -2.28(19) |
| C(5)—C(6)—C(12)—C(11) | -1.94(19) |
| C(7)—C(6)—C(12)—C(11) | 176.67(12) |
| C(2)—N(3)—C(15)—C(20) | -72.70(16) |
| C(2)—N(3)—C(15)—C(16) | 114.22(14) |
| C(20)—C(15)—C(16)—C(17) | -0.3(2) |
| N(3)—C(15)—C(16)—C(17) | 172.76(12) |
| C(20)—C(15)—C(16)—C(21) | -178.86(13) |
| N(3)—C(15)—C(16)—C(21) | -5.84(19) |
| C(15)—C(16)—C(17)—C(18) | 0.7(2) |
| C(21)—C(16)—C(17)—C(18) | 179.27(14) |
| C(16)—C(17)—C(18)—C(19) | -0.5(2) |
| C(16)—C(17)—C(18)—C(22) | -179.15(14) |
| C(17)—C(18)—C(19)—C(20) | -0.2(2) |
| C(22)—C(18)—C(19)—C(20) | 178.52(14) |
| C(18)—C(19)—C(20)—C(15) | 0.6(2) |
| C(18)—C(19)—C(20)—C(23) | -175.26(14) |
| C(16)—C(15)—C(20)—C(19) | -0.4(2) |
| N(3)—C(15)—C(20)—C(19) | -173.37(12) |
| C(16)—C(15)—C(20)—C(23) | 175.44(13) |
| N(3)—C(15)—C(20)—C(23) | 2.4(2) |
| C(1)—N(2)—C(24)—C(25) | 85.94(13) |
| C(2)—N(2)—C(24)—C(25) | -89.49(13) |
| C(26)—N(4)—C(25)—C(24) | -105.34(14) |
| N(2)—C(24)—C(25)—N(4) | 177.45(10) |
| C(25)—N(4)—C(26)—O(4) | -5.4(2) |
| C(25)—N(4)—C(26)—N(5) | 173.13(12) |

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Those skilled in the art will recognize, or be able to ascertain using no more than routine experimentation, many equivalents of the specific embodiments of the invention described herein. Such equivalents are intended with be encompassed by the following claims.

What is claimed is:

1. A compound N-{2-[(2E)-2-(mesitylimino)-9,10-dimethoxy-4-oxo-6,7-dihydro-2H-pyrimido[6,1-a]-isoquinolin-3(4H)-yl]ethyl}urea, in the form of a crystalline solid consisting of greater than 99% by weight of N-{2-[(2E)-2-(mesitylimino)-9,10-dimethoxy-4-oxo-6,7-dihydro-2H-pyrimido[6,1-a]-isoquinolin-3(4H)-yl]ethyl}urea, at least 95% in the polymorphic form of a thermodynamically stable polymorph (I) of N-{2-[(2E)-2-(mesitylimino)-9,10-dimethoxy-4-oxo-6,7-dihydro-2H-pyrimido[6,1-a]-isoquinolin-3(4H)-yl]ethyl}urea, said polymorph (I) having the following structural parameters obtained by single crystal analysis:

| | | |
|---|---|---|
| Wavelength | 0.71073 Å | |
| Crystal system | Triclinic | |
| Space group | P-1 | |
| Unit cell dimensions | a = 8.1246(4) Å | α = 91.583(4)°. |
| | b = 11.4573(5) Å | β = 90.299(4)°. |
| | c = 13.2398(6) Å | γ = 99.628(4)°. |
| Volume | 1214.56(10) Å$^3$. | |
| Z | 2. | |

2. A crystalline polymorph (I) of N-{2-[(2E)-2-(mesitylimino)-9,10-dimethoxy-4-oxo-6,7-dihydro-2H-pyrimido[6,1-a]-isoquinolin-3(4H)-yl]ethyl}urea having a powder X-ray diffraction pattern comprising characteristic peaks, in terms of 2θ, at 10.1° and 12.9°.

3. The polymorph of claim 2 wherein said powder X-ray diffraction pattern further comprises characteristics peaks, in terms of 2θ, at 15.3° and 17.6°.

4. The polymorph of claim 2 wherein said powder X-ray diffraction pattern comprises at least 5 characteristic peaks, in terms of 2θ, selected from 6.4°, 10.1°, 12.6°, 12.9°, 13.6°, 14.2°, 14.7°, 15.3°, 15.4°, 15.8°, 17.0°, 17.6°, 18.9°, 20.9°, 22.4°, 22.8°, and 28.7°.

5. A solid composition comprising the polymorph of claim 2 and a pharmaceutically acceptable carrier.

6. The composition of claim 5 wherein at least 50% by weight of total N-{2-[(2E)-2-(mesitylimino)-9,10-dimethoxy-4-oxo-6,7-dihydro-2H-pyrimido[6,1-a]-isoquinolin-3(4H)-yl]ethyl}urea in said composition is present as said polymorph.

7. The composition of claim 5 wherein at least 70% by weight of total N-{2-[(2E)-2-(mesitylimino)-9,10-dimethoxy-4-oxo-6,7-dihydro-2H-pyrimido[6,1-a]-isoquinolin-3(4H)-yl]ethyl}urea in said composition is present as said polymorph.

8. The composition of claim 5 wherein at least 90% by weight of total N-{2-[(2E)-2-(mesitylimino)-9,10-dimethoxy-4-oxo-6,7-dihydro-2H-pyrimido[6,1-a]-isoquinolin-3(4H)-yl]ethyl}urea in said composition is present as said polymorph.

9. The composition of claim 5 wherein at least 97% by weight of total N-{2-[(2E)-2-(mesitylimino)-9,10-dimethoxy-4-oxo-6,7-dihydro-2H-pyrimido[6,1-a]-isoquinolin-3(4H)-yl]ethyl}urea in said composition is present as said polymorph.

10. A solid composition comprising the polymorph of claim 1 and one or more additional compounds.

11. The solid composition of claim 10, wherein the additional compound is a known therapeutic.

12. A process for preparing the polymorph of claim 2 comprising:
(a) combining N-{2-[(2E)-2-(mesitylimino)-9,10-dimethoxy-4-oxo-6,7-dihydro-2H-pyrimido[6,1-a]-isoquinolin-3(4H)-yl]ethyl}urea with a solvent to form a mixture, and
(b) heating said mixture at or above a temperature of about 50° C. for a time and under conditions suitable for forming said polymorph.

13. A process for preparing the polymorph of claim 2 comprising:
(a) combining N-{2-[(2E)-2-(mesitylimino)-9,10-dimethoxy-4-oxo-6,7-dihydro-2H-pyrimido[6,1-a]-isoquinolin-3(4H)-yl]ethyl}urea with a solvent to form a mixture,
(b) filtering said mixture to form a filtered mixture
(c) heating said filtered mixture at or above a temperature of about 55° C. for a time and under conditions suitable for forming said polymorph; and
(d) filtering and drying said polymorph.

14. The process of claim 12, wherein the solvent is DMSO, ethanol, methanol, isopropanol, hexanes, pentane, ethyl acetate, dichloromethane, or chloroform.

15. The process of claim 14, wherein the solvent is DMSO or ethanol.

16. The process of claim 12 wherein said filtered mixture is maintained at or above a temperature of about 50° C. for about 24 to 96 hours.

17. The process of claim 16, wherein said filtered mixture is maintained at or above a temperature of about 50° C. for about 72 hours.

18. The process of claim 12 wherein said filtered mixture is maintained at or above a temperature of about 55° C. for about 24 to 96 hours.

19. The process of claim 16, wherein said filtered mixture is maintained at or above a temperature of about 55° C. for about 72 hours.

20. The process of claim 12 wherein said mixture is dried in vacuo at between 25 and 50° C.

21. The process of claim 20 wherein said mixture is dried in vacuo at 40° C.

22. The polymorph of claim 2, prepared by the method comprising
(a) combining N-{2-[(2E)-2-(mesitylimino)-9,10-dimethoxy-4-oxo-6,7-dihydro-2H-pyrimido[6,1-a]-isoquinolin-3(4H)-yl]ethyl}urea with a solvent to form a mixture, and
(b) heating said mixture at or above a temperature of 50° C. for a time and under conditions suitable for forming said polymorph.

23. The polymorph of claim 2, prepared by the method comprising
(a) combining N-{2-[(2E)-2-(mesitylimino)-9,10-dimethoxy-4-oxo-6,7-dihydro-2H-pyrimido[6,1-a]-isoquinolin-3(4H)-yl]thyl}urea with a solvent to form a mixture,
(b) filtering said mixture to form a filtered mixture,
(c) heating said filtered mixture at or above a temperature of 55° C. for a time and under condition suitable for forming said polymorph; and
(d) filtering and drying said polymorph.

24. A method to treat chronic obstructive pulmonary disease (COPD), in a mammal suffering from COPD, which method comprises administering to said mammal an effective amount of a crystalline polymorph of N-{2-[(2E)-2-(mesitylimino)-9,10-dimethoxy-4-oxo-6,7-dihydro-2H-pyrimido[6,1-a]-isoquinolin-3(4H)-yl]ethyl}urea.

25. The method of claim 24, wherein the mammal is a human.

* * * * *